United States Patent
Ueda

(10) Patent No.: US 12,075,153 B2
(45) Date of Patent: Aug. 27, 2024

(54) IMAGING APPARATUS AND CONTROL METHOD OF THE SAME

(71) Applicant: CANON KABUSHIKI KAISHA, Tokyo (JP)

(72) Inventor: Kiyoto Ueda, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 114 days.

(21) Appl. No.: 18/056,638

(22) Filed: Nov. 17, 2022

(65) Prior Publication Data

US 2023/0164428 A1 May 25, 2023

(30) Foreign Application Priority Data

Nov. 25, 2021 (JP) .................. 2021-191533

(51) Int. Cl.
| | |
|---|---|
| *H04N 23/63* | (2023.01) |
| *G16H 30/40* | (2018.01) |
| *H04N 5/92* | (2006.01) |
| *H04N 23/62* | (2023.01) |
| *H04N 23/667* | (2023.01) |
| *G06K 7/14* | (2006.01) |

(52) U.S. Cl.
CPC ........... *H04N 23/633* (2023.01); *G16H 30/40* (2018.01); *H04N 5/9201* (2013.01); *H04N 23/62* (2023.01); *H04N 23/632* (2023.01); *H04N 23/667* (2023.01); *G06K 7/1413* (2013.01); *G06K 7/1417* (2013.01)

(58) Field of Classification Search
CPC ...... H04N 23/62; H04N 23/63; H04N 23/631; H04N 23/633; H04N 23/667
USPC ........................................................ 348/220.1
See application file for complete search history.

(56) References Cited

U.S. PATENT DOCUMENTS

| | | | |
|---|---|---|---|
| 5,913,086 | A | 6/1999 | Kawamura |
| 10,790,051 | B2 | 9/2020 | Toyoda et al. |
| 11,165,964 | B2 | 11/2021 | Ogawa |
| 2007/0182846 | A1 | 8/2007 | Uchida |
| 2016/0078596 | A1 | 3/2016 | Ohashi |
| 2017/0272660 | A1* | 9/2017 | Ishihara ............... G06T 3/04 |

(Continued)

FOREIGN PATENT DOCUMENTS

| | | |
|---|---|---|
| JP | H08-220582 A | 3/1996 |
| JP | 2012029056 A | 2/2012 |

(Continued)

*Primary Examiner* — Anthony J Daniels
(74) *Attorney, Agent, or Firm* — Canon U.S.A., Inc. IP Division

(57) ABSTRACT

An imaging apparatus includes a display control unit configured to perform control to display, on a display unit, a live image captured by the imaging unit and medical information, and a control unit configured to associate image data obtained by the imaging unit and the medical information in accordance with a full press operation on a shutter button, wherein the display control unit performs control, in accordance with a predetermined user operation, to switch between first display of displaying the medical information together with a live image and second display of displaying an imaging parameter related to image capturing together with a live image, and wherein the display control unit performs control, in accordance with a half press operation on the shutter button different from the predetermined user operation, to switch display to the first display.

17 Claims, 17 Drawing Sheets

(56) References Cited

U.S. PATENT DOCUMENTS

| | | | |
|---|---|---|---|
| 2019/0014246 A1 | 1/2019 | Furukawa | |
| 2019/0260944 A1* | 8/2019 | Ogawa | H04N 23/65 |
| 2019/0341129 A1 | 11/2019 | Toyoda et al. | |
| 2020/0066394 A1 | 2/2020 | Toyoda et al. | |
| 2020/0228727 A1* | 7/2020 | Zheng | H04N 23/631 |
| 2021/0280300 A1 | 9/2021 | Hikosaka | |

FOREIGN PATENT DOCUMENTS

| | | | | |
|---|---|---|---|---|
| JP | 2016059534 A | * | 4/2016 | A61B 6/4233 |
| JP | 2019145984 A | | 8/2019 | |

* cited by examiner

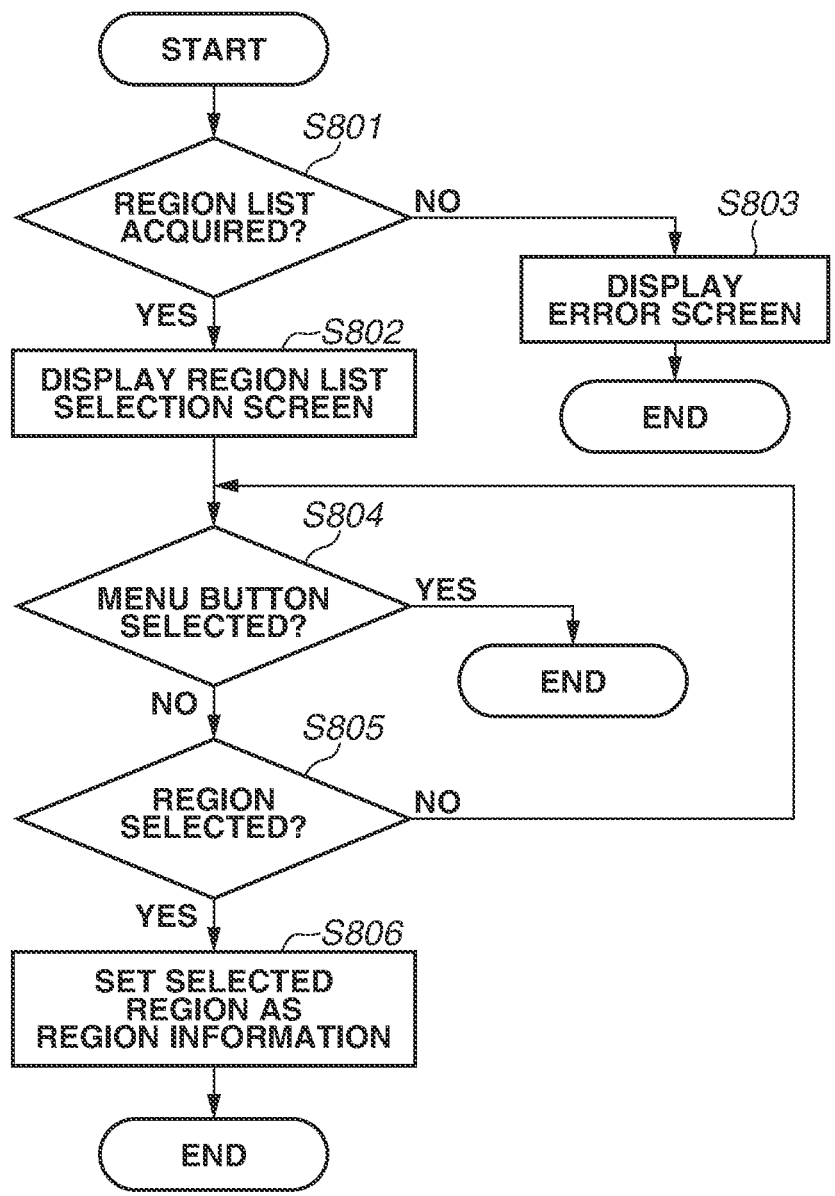

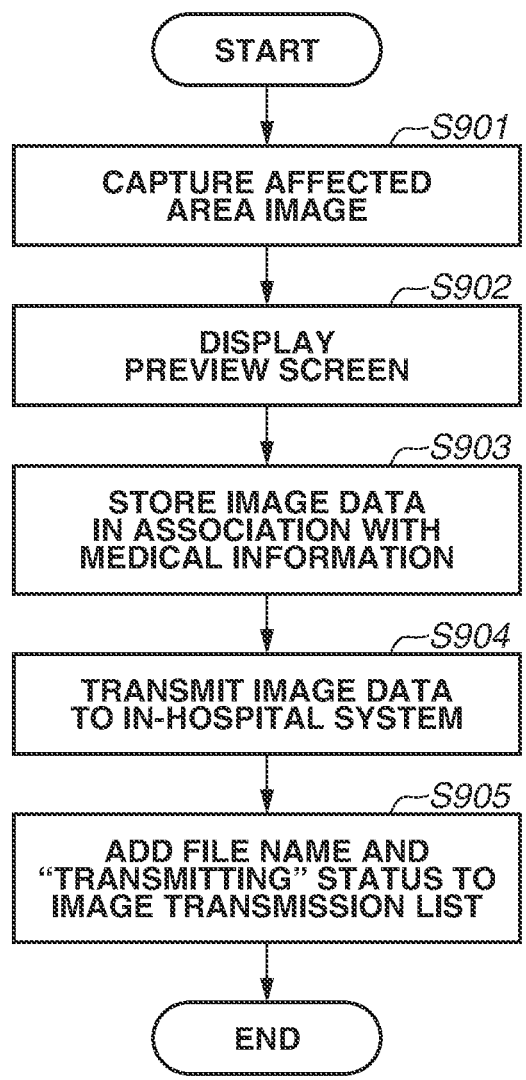

IMAGING APPARATUS AND CONTROL METHOD OF THE SAME

BACKGROUND OF THE INVENTION

Field of the Invention

A present invention relates to an imaging apparatus and a control method of an imaging apparatus.

Description of the Related Art

Techniques of associating an image and information regarding a subject of the image have been proposed. Japanese Patent Application Laid-Open No. 2019-145984 discusses an imaging apparatus that captures an image of a code, analyzes the code, acquires patient information corresponding to the code from a database, superimposes the patient information on a live view image display, and records obtained image data in association with the patient information.

SUMMARY OF THE INVENTION

The present invention is directed to an imaging apparatus in which medical information and an imaging parameter are provided for a user to perform a confirmation and the medical information is provided for the user to perform a confirmation before image capturing of image data.

According to an aspect of the present invention, an imaging apparatus includes a memory and at least one processor which function as a display control unit configured to perform control to display, on a display unit, a live image captured by the imaging unit and medical information, and a control unit configured to associate image data obtained by the imaging unit and the medical information in accordance with a full press operation on a shutter button, wherein the display control unit performs control, in accordance with a predetermined user operation, to switch between first display of displaying the medical information together with a live image and second display of displaying an imaging parameter related to image capturing together with a live image, and wherein the display control unit performs control, in accordance with a half press operation on the shutter button different from the predetermined user operation, to switch display to the first display.

Further features of the present invention will become apparent from the following description of example embodiments with reference to the attached drawings.

BRIEF DESCRIPTION OF THE DRAWINGS

FIG. 8 is a flowchart of the region information acquisition processing.

FIG. 9 is a flowchart of affected area image capturing processing.

DESCRIPTION OF THE EMBODIMENTS

Hereinafter, an example embodiment of the present invention will be described with reference to the drawings.
<External View of Imaging Apparatus 100>

Figure 1A:
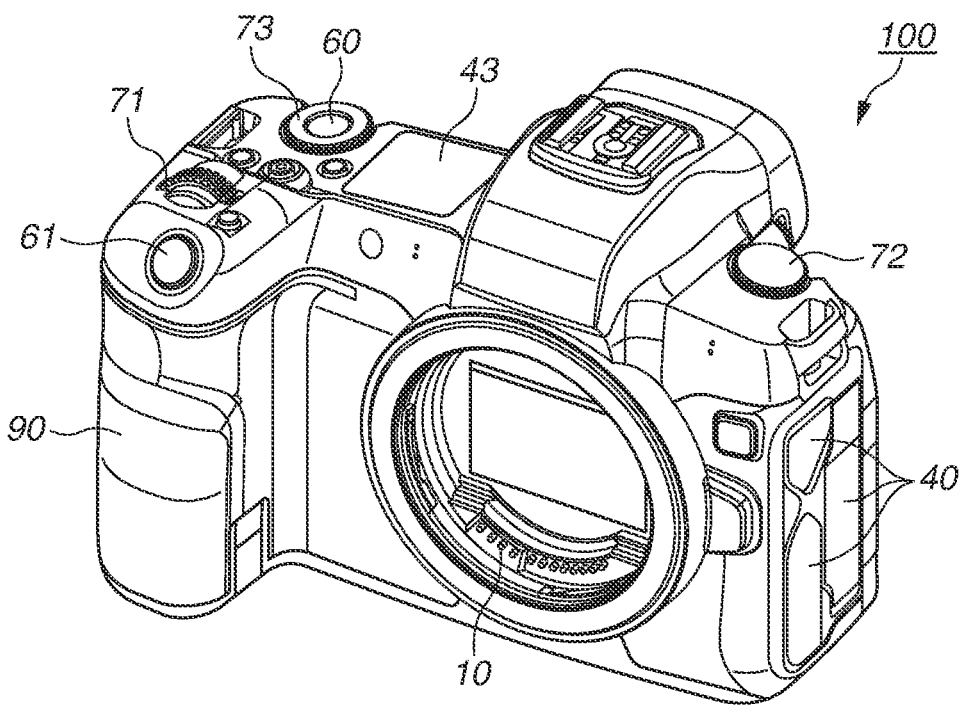
FIGS. 1A and 1B are external views of an imaging apparatus.
Figure 1B:
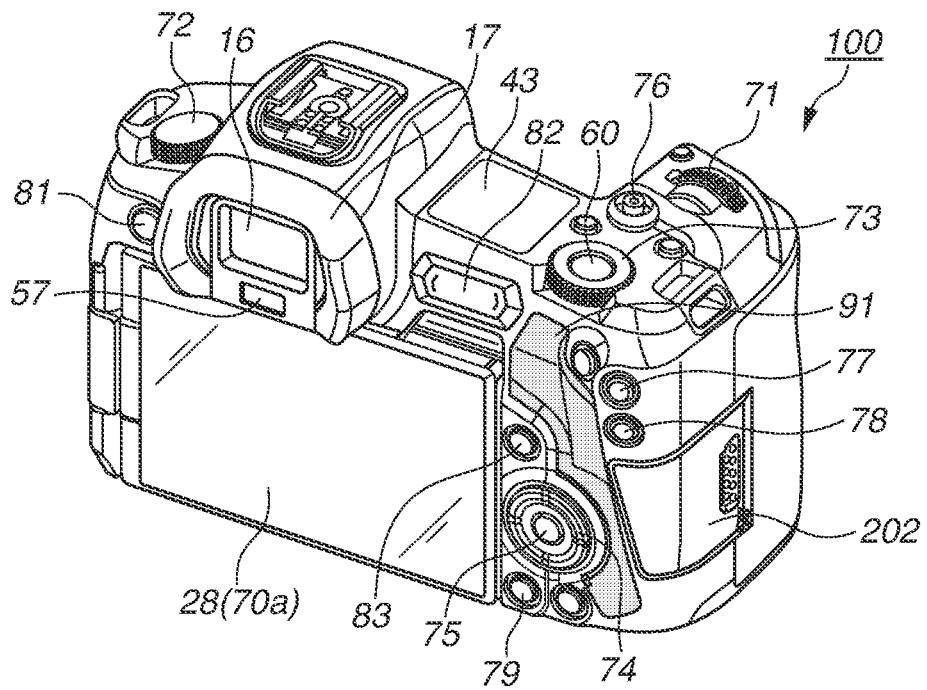

FIGS. 1A and 1B are external views of a digital camera (imaging apparatus) 100 serving as an example of an apparatus (electronic device) to which the present invention can be applied. FIG. 1A is a front side perspective view of the digital camera 100 and FIG. 1B is a back side perspective view of the digital camera 100.

A display unit 28 disposed on the back surface of the digital camera 100 displays images and various types of information. A touch panel 70a detects touch operations on a display surface (touch operation surface) of the display unit 28. A viewfinder external display unit 43 disposed on a top surface of the digital camera 100 displays various setting values, such as a shutter speed and an aperture value, of the digital camera 100. A shutter button 61 is an operation member for use in issuing an image capturing instruction. A mode selection switch 60 is an operation member for use in switching a mode between various modes. A terminal cover 40 protects a connector (not illustrated) for, for example, a connection cable that connects the digital camera 100 to an external device.

A main electronic dial 71 is a rotary operation member. A rotation operation on the main electronic dial 71 moves a selection frame (cursor) and changes setting values, such as a shutter speed and an aperture value, in accordance with a display state. A power switch 72 is an operation member for use in switching between ON and OFF of the power of the digital camera 100. A sub electronic dial 73 is a rotary operation member. A rotation operation on the sub electronic dial 73 moves a selection frame (cursor), changes setting values, such as a shutter speed and an aperture value, and feeds images, in accordance with a display state. A four directional key (cross key) 74 is an operation member which includes upper, lower, left, and right portions capable of being individually pressed, and an operation on the four directional key 74 moves a selection frame (cursor) and issues an execution instruction of processing corresponding to a pressed portion of the four directional key 74, in accordance with a display state. A SET button 75 is another example of an operation member and is a push button for mainly use in determination of a selected item.

Other examples of operation members, which may be buttons or keys, are described in the following. A movie button 76 is for use in issuing start and stop instructions of moving image capturing (recording). An autoexposure (AE) lock button 77 is a push button. A pressing operation on the AE lock button 77 in an imaging standby state fixes an exposure state. An enlargement button 78 is an operation button for use in switching between ON and OFF of an enlarged mode in live view display (LV display) in an image capturing mode. An operation on the main electronic dial 71 after the enlarged mode is turned ON enlarges or reduces a live view image (live image, LV image). In a reproduction mode, the enlargement button 78 functions as an operation button to enlarge a reproduced image and to increase an enlargement ratio of the reproduced image. A reproduction button 79 is an operation button for use in switching between the image capturing mode and the reproduction mode. A pressing operation on the reproduction button 79 while the digital camera 100 is in the image capturing mode shifts the digital camera 100 to the reproduction mode, and a latest image among images recorded on a recording medium 200 (to be described below) is displayed on the display unit 28. A MENU button 81 is a push button that is used in an instruction operation to display a menu screen. When the MENU button 81 is pressed, the menu screen on which various settings are set is displayed on the display unit 28. The user can intuitively perform various settings using the menu screen displayed on the display unit 28, the four directional key 74, and the SET button 75.

A touch bar 82 (multifunction bar: M-Fn bar) is a linear touch operation member (line touch sensor) for use in receiving a touch operation. The touch bar 82 is disposed at a position touch-operable (touchable) by a right thumb in a state in which a grip portion 90 is gripped by a right hand (gripped by a right little finger, a right ring finger, and a right middle finger) in a manner such that a right index finger can press the shutter button 61. In other words, the touch bar 82 is disposed at a position operable in a state in which the user is looking into a viewfinder with his/her eye being kept close to an eyepiece unit 16 and is holding the digital camera 100 in a manner ready to press the shutter button 61 (image capturing orientation). The touch bar 82 is a reception unit that receives, for example, a tap operation on the touch bar 82 (an operation of touching the touch bar 82 with a finger and detaching the finger within a predetermined time period without moving a touch position) and a left-right slide operation on the touch bar 82 (an operation of touching the touch bar 82 and then moving a touch position while touching the touch bar 82). The touch bar 82 is an operation member different from the touch panel 70a and does not include a display function.

A display switching button 83 is an example of an operation member and is a push button for use in switching information that is superimposed on a LV image in LV display in the image capturing mode. When a medical mode is ON, the display switching button 83 functions as a member for use in switching information to be displayed between medical information and imaging parameter information. When the medical mode is OFF, the display switching button 83 functions as a member for use in switching display between several patterns of imaging parameter information.

A communication terminal 10 of the digital camera 100 is a communication terminal for use in communication with a lens unit 150 (detachable) to be described below. The eyepiece unit 16 is an eyepiece unit of an eyepiece viewfinder 17 (look-in viewfinder). The user can visually check a video displayed on an internal electric viewfinder (EVF) 29 via the eyepiece unit 16. An eye approximation detection unit 57 is an eye approximation detection sensor that detects whether an eye of a user (photographer) approaches the eyepiece unit 16. A lid 202 is a lid of a slot storing the recording medium 200 (to be described below). The grip portion 90 is a holding portion having a shape that can be easily grasped by a right hand when the user holds the digital camera 100. The shutter button 61 and the main electronic dial 71 are disposed at positions operable by the right index finger in a state in which the user holds the digital camera 100 by grasping the grip portion 90 with the right little finger, the right ring finger, and the right middle finger. In addition, the sub electronic dial 73 and the touch bar 82 are disposed at positions operable by the right thumb in the above-described holding state. A thumb rest portion 91 (thumb standby position) is a grip member disposed at a position on the rear side of the digital camera 100 where the user can naturally place his/her thumb of the right hand gripping the grip portion 90 in a state in which the user operates none of the operation members. The thumb rest portion 91 is formed of rubber member to enhance holding force (grip force).

<Configuration Block Diagram of Imaging Apparatus 100>

Figure 2:
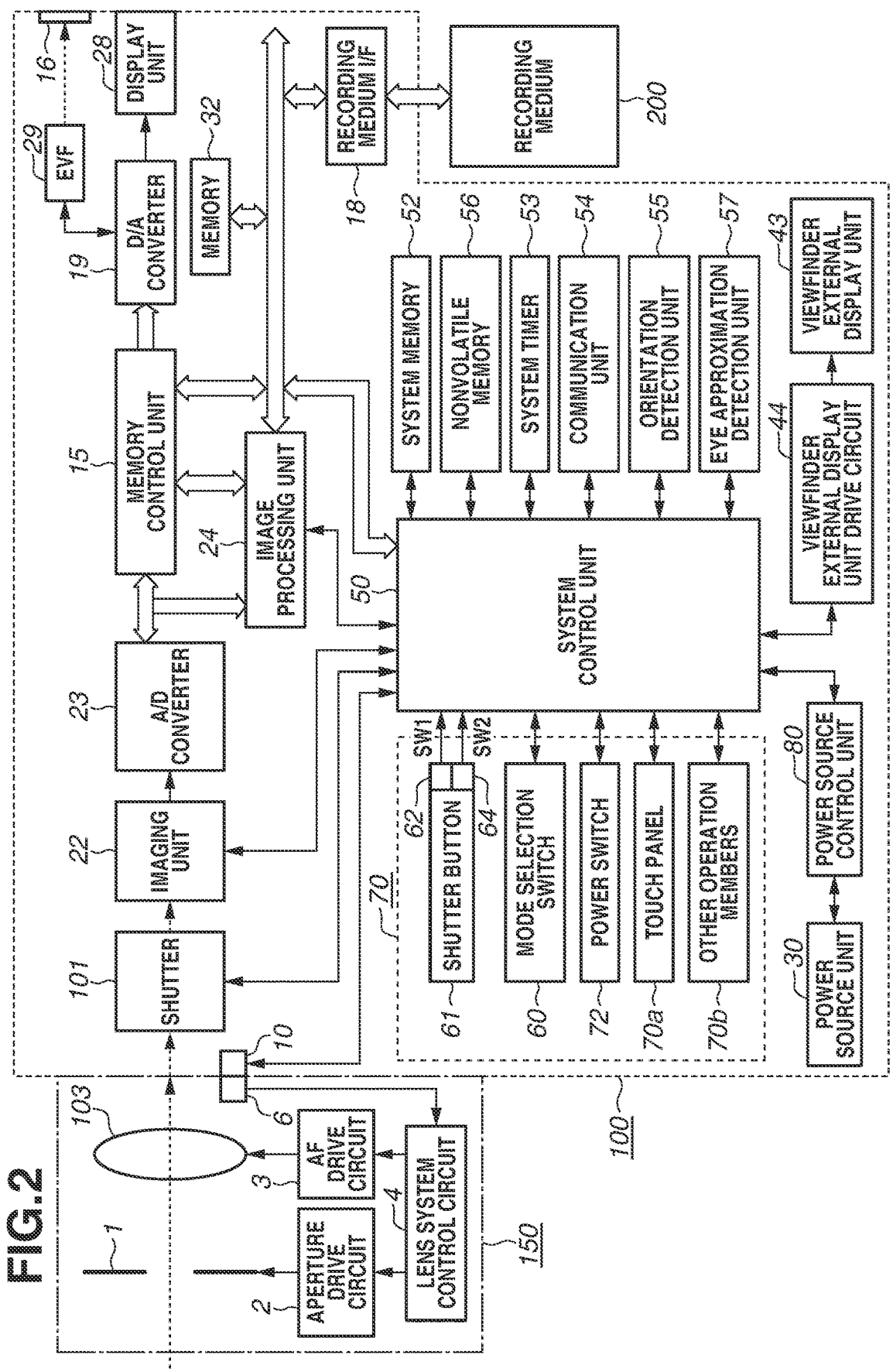
FIG. 2 is a block diagram of the imaging apparatus.

FIG. 2 is a block diagram illustrating a configuration example of the digital camera 100 (imaging apparatus). The lens unit 150 is a lens unit including an interchangeable imaging lens. While a lens 103 normally includes a plurality of lenses, the plurality of lenses is illustrated as one lens in FIG. 2 for the sake of simplification. A communication terminal 6 of the lens unit 150 is a communication terminal for use in communication with the digital camera 100. The communication terminal 10 of the digital camera 100 is the communication terminal for use in communication with the lens unit 150. The lens unit 150 communicates with a system control unit 50 via the communication terminals 6 and 10. Then, the lens unit 150 controls an aperture 1 via an aperture drive circuit 2 using a lens system control circuit 4 provided inside the lens unit 150. The lens unit 150 also executes focusing by displacing the position of the lens 103 via an autofocus (AF) drive circuit 3 using the lens system control circuit 4.

A shutter 101 is a focal plane shutter with which exposure time of an imaging unit 22 can be controlled under the control of the system control unit 50.

The imaging unit 22 is an image sensor including a charge-coupled device (CCD) sensor or a complementary metal-oxide semiconductor (CMOS) sensor that converts an optical image into an electrical signal. The imaging unit 22 can include an imaging plane phase difference sensor for outputting defocus amount information to the system control unit 50. An analog-to-digital (A/D) converter 23 converts an analog signal output from the imaging unit 22 into a digital signal.

An image processing unit 24 performs predetermined processing (pixel interpolation, resize processing, such as reduction, color conversion processing, etc.) on data from the A/D converter 23 or data from a memory control unit 15. The image processing unit 24 also performs predetermined calculation processing using data of a captured image. Based on the calculation result obtained by the image processing unit 24, the system control unit 50 performs exposure control and ranging control. Through-the-lens (TTL) system AF processing, AE processing, and electronic flash pre-emission (EF) processing are thus performed. The image processing unit 24 further performs predetermined calculation processing using data of a captured image, and also performs TTL system automatic white balance (AWB) processing, based on the obtained calculation result.

Data outputted from the A/D converter 23 is written into a memory 32 via the image processing unit 24 and the memory control unit 15. Alternatively, data outputted from the A/D converter 23 is written into the memory 32 via the memory control unit 15 not via the image processing unit 24. The memory 32 stores image data, obtained by the imaging unit 22 and converted by the A/D converter 23 into digital data, and image data to be displayed on the display unit 28 or the EVF 29. The memory 32 has a storage capacity sufficient for storing a predetermined number of still images and a moving image and voice having a predetermined time length.

The memory 32 also serves as a memory (video memory) for image display. A digital-to-analog (D/A) converter 19 converts display image data stored in the memory 32 into an analog signal and supplies the analog signal to the display unit 28 or the EVF 29. Display image data written into the memory 32 in this manner is displayed on the display unit 28 and the EVF 29 via the D/A converter 19. The display unit 28 and the EVF 29 are displays, such as a liquid crystal display (LCD) or an organic electroluminescence (EL) display, and perform display in accordance with an analog signal from the D/A converter 19. Digital signals A/D-converted by the A/D converter 23 and stored in the memory 32 are converted into analog signals by the D/A converter 19, and the analog signals are sequentially transferred to the display unit 28 and the EVF 29 and displayed on the display unit 28 and the EVF 29. Live view display (LV) can be thus performed. Hereinafter, an image displayed in live view display will be referred to as a live view image (LV image) or live image.

The system control unit 50 is a control unit including at least one processor and/or at least one circuit and controls the entire operation of the digital camera 100. The system control unit 50 is a processor, and is a circuit. By executing a program recorded on a nonvolatile memory 56, the system control unit 50 implements each piece of processing in the present example embodiment, which will be described below. The system control unit 50 also performs display control by controlling the memory 32, the D/A converter 19, the display unit 28, and the EVF 29.

For example, a random access memory (RAM) serves as a system memory 52. The system control unit 50 loads constants for operating the system control unit 50, variables, and programs read out from the nonvolatile memory 56, into the system memory 52.

The nonvolatile memory 56 is an electrically-erasable/recordable memory, and is an electrically erasable programmable read-only memory (EEPROM), for example. Constants for operating the system control unit 50 and programs are recorded on the nonvolatile memory 56. The programs refer to programs for various processes of flowcharts to be described below in the present example embodiment.

A system timer 53 is a time measuring unit for measuring a time to be used for various types of control and a time of a built-in clock.

Figure 15:
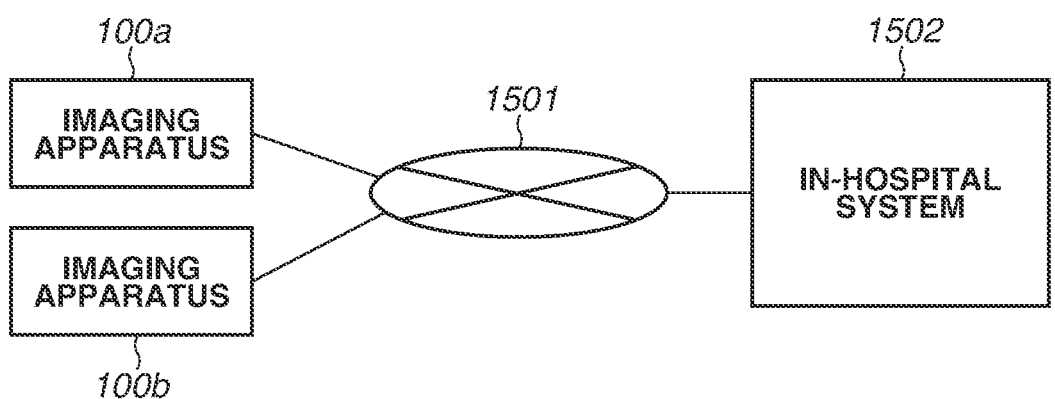
FIG. 15 is a diagram illustrating a network system of an in-hospital system and an imaging apparatus.

A communication unit 54 transmits and receives video signals and audio signals to and from an external device connected wirelessly or via a cable. The communication unit 54 can also be connected with a wireless local area network (LAN) and the Internet. The communication unit 54 can also communicate with an external device via Bluetooth® or Bluetooth® Low Energy. The communication unit 54 can transmit an image (including a LV image) captured by the imaging unit 22 and an image recorded on the recording medium 200. In the present example embodiment, the digital camera 100 can communicate with an in-hospital system (medical system of, for example, electronic medical charts and a medical accounting system) serving as an external device, via a server. The digital camera 100 can receive, from the in-hospital system, medical information (including patient information, user information, affected area information), image data, and other various types of information. As illustrated in FIG. 15, an in-hospital network system within a hospital includes a server 1501 and an in-hospital system 1502. A plurality of digital cameras (imaging apparatuses) 100a and 100b can connect to the server 1501 via the communication units 54 of the digital cameras, and acquire various types of information from the in-hospital system 1502. In the present example embodiment, the server 1501 different from the in-hospital system 1502 is used. Because the communication is executed via the server 1501, information transmission and reception between the imaging apparatuses 100 and the in-hospital system 1502 can be implemented without extensive changes in the in-hospital system 1502. In addition, the imaging apparatuses 100 can directly connect to the in-hospital system 1502 not via the server 1501. Alternatively, the function of the server 1501 can be provided in the in-hospital system 1502. In the above-described manner, an imaging apparatus 100 according to an example embodiment of the present invention can connect with a predetermined specific system (server 1501 or in-hospital system 1502) and acquire patient information and information regarding a doctor and/or nurse from electronic medical charts or a medical accounting system of the in-hospital system 1502. While, in the present example embodiment, the in-hospital system 1502 will be described as a medical system, the medical system needs not be installed inside a hospital. The medical system can be a system in which the imaging apparatuses 100 communicate with a server or a medical system that is provided on the outside of a hospital, via the internet.

An orientation detection unit 55 detects the orientation of the digital camera 100 with respect to a direction of gravitational force. Based on the orientation detected by the orientation detection unit 55, determination of whether an image captured by the imaging unit 22 is an image captured with the digital camera 100 being held in a landscape direction or an image captured with the digital camera 100 being held in a portrait direction can be performed. The system control unit 50 can add orientation information corresponding to the orientation detected by the orientation detection unit 55, to an image file of an image captured by the imaging unit 22, or rotate an image and store the rotated image. As the orientation detection unit 55, an acceleration sensor or a gyro sensor can be used. The acceleration sensor or the gyro sensor serving as the orientation detection unit 55 can also be used to detect the movement (pan, tilt, lifting, whether stationary, etc.) of the digital camera 100.

The eye approximation detection unit 57 is an eye approximation detection sensor that detects an approximation and a separation of an eye (object) with respect to the eyepiece unit 16 of an eyepiece viewfinder 17 (hereinafter, simply described as "viewfinder") (approximation detection). In accordance with the state detected by the eye approximation detection unit 57, the system control unit 50 switches the display (displayed state)/nondisplay (non-displayed state) of the display unit 28 and the EVF 29. More specifically, in a case where the digital camera 100 is at least in an imaging standby state and a switching setting of a display destination is set to an automatic switching setting, the display destination is set to the display unit 28 and the display is set to ON, and the EVF 29 is set to the non-displayed state, during the separation of an eye from the eyepiece unit 16. Alternatively, in a case where an eye approaches the eyepiece unit 16, the display destination is set to the EVF 29 and the display is set to ON, and the display unit 28 is set to the non-displayed state. For example, an infrared light proximity sensor can be used as the eye approximation detection unit 57. The eye approximation detection unit 57 can detect an approximation of any object to the eyepiece unit 16 of the viewfinder 17 incorporating the EVF 29. In a case where an object approaches, infrared light projected from a light projection unit (not illustrated) of the eye approximation detection unit 57 is reflected on the object and received by a light receiving unit (not illustrated) of the infrared light proximity sensor. Based on an amount of the received infrared light, a distance between the object and the eyepiece unit 16 (eye approximation distance) can also be determined. In the above-described manner, the eye approximation detection unit 57 performs eye approximation detection of detecting an approximation distance of an object to the eyepiece unit 16. In a case where an object that approaches the eyepiece unit 16 at less than or equal to a predetermined distance away from the eyepiece unit 16 in a non-contact state (separated state) is detected, an approximation of the eye is detected. In a case where an object of which approximation to the eyepiece unit 16 had been detected is separated from the eyepiece unit 16 by a predetermined distance or more in a contact state (approximated state), the separation of the eye is detected. A threshold for detecting the approximation of the eye and a threshold for detecting the separation of the eye may be different from each other by providing a hysteresis, for example. In addition, after the approximation of the eye is detected, the contact state is maintained until a separation of the eye is detected. After the separation of the eye is detected, the non-contact state is kept until an approximation of the eye is detected. The infrared light proximity sensor is an example, and a different sensor can be employed as the eye approximation detection unit 57 as long as the sensor can detect the proximity of an eye or an object that can be considered as an eye in the detection of the proximity.

Various camera setting values including a shutter speed and an aperture value are displayed on the viewfinder external display unit 43 via a viewfinder external display unit drive circuit 44.

A power source control unit 80 includes a battery detection circuit, a direct current (DC)-DC converter, and a switch circuit for switching a block to be supplied with power. The power source control unit 80 detects whether or not a battery is attached, the type of the battery, and remaining battery capacity. In addition, the power source control unit 80 controls the DC-DC converter, based on the detection result and an instruction from the system control unit 50, and supplies necessary voltage to components including the recording medium 200 for a necessary time period. A power source unit 30 includes a primary battery, such as an alkaline battery and a lithium battery, a secondary battery, such as a nickel-cadmium (NiCd) battery, a nickel-metal hydride (NiMH) battery, and a lithium (Li) battery, and an alternating current (AC) adapter.

A recording medium interface (I/F) 18 is an interface to the recording medium 200, such as a memory card and a hard disc. The recording medium 200 is a recording medium, such as a memory card, for recording a captured image and includes a semiconductor memory or a magnetic disc.

An operation unit 70 is an input unit for receiving operations (user operations) from the user and is for use in inputting various operation instructions to the system control unit 50. As illustrated in FIG. 2, the operation unit 70 includes the shutter button 61, the mode selection switch 60, the power switch 72, the touch panel 70a, and other operation members 70b. The other operation members 70b include the main electronic dial 71, the sub electronic dial 73, the four directional key 74, the SET button 75, the movie button 76, the AE lock button 77, the enlargement button 78, the reproduction button 79, the MENU button 81, the touch bar 82, and the display switching button 83.

The shutter button 61 includes a first shutter switch 62 and a second shutter switch 64. The first shutter switch 62 is turned ON in the middle of an operation on the shutter button 61. The first shutter switch 62 is turned ON by a half pressing operation (i.e. an imaging preparation instruction) and outputs a first shutter switch signal SW1. In accordance with the first shutter switch signal SW1, the system control unit 50 starts imaging preparation processing, such as AF processing, AE processing, AWB processing, or EF processing.

The second shutter switch 64 is turned ON upon completion of an operation on the shutter button 61. The second shutter switch 64 is turned ON by a full pressing operation (i.e. imaging instruction) and outputs a second shutter switch signal SW2. In accordance with the second shutter switch signal SW2, the system control unit 50 starts a series of imaging processes starting from signal readout from the imaging unit 22 up to writing of a generated image file including a captured image into the recording medium 200.

The mode selection switch 60 switches an operation mode of the system control unit 50 to either mode of a still image capturing mode, a moving image capturing mode, and a reproduction mode. The still image capturing mode includes modes, such as an automatic image capturing mode, an automatic scene determination mode, a manual mode, an aperture priority mode (Av mode), a shutter speed priority mode (Tv mode), and a program AE mode (P mode). The still image capturing mode further includes modes, such as various scene modes each having a different image capturing setting for a corresponding image capturing scene and a custom mode. The user uses the mode selection switch 60 to directly switch an operation mode to any one of the modes. Alternatively, an operation mode can be switched in the following manner. The mode selection switch 60 switches a screen to a list screen of image capturing modes, and then any one of a plurality of displayed modes is selected using another operation member so that an operation mode is switched to the selected mode. Similar to the still image capturing mode, the moving image capturing mode can include a plurality of modes.

The touch panel 70a is a touch sensor that detects various touch operations on the display surface of the display unit 28 (operation surface of the touch panel 70a). The touch panel 70a and the display unit 28 can be integrally formed. For example, the touch panel 70a is attached to a top layer of the display surface of the display unit 28 in a manner such that light transmittance does not disturb display on the display unit 28. Then, an input coordinate on the touch panel 70a and a display coordinate on the display surface of the display unit 28 are associated with each other. This structure can provide a graphical user interface (GUI) that performs display as if the user could directly operate a screen displayed on the display unit 28.

The system control unit 50 can detect the following operations performed on the touch panel 70*a* or the following state of the touch panel 70*a*.

An operation of a finger or a stylus that has not been in touch with the touch panel 70*a* newly touching the touch panel 70*a*, i.e., the start of a touch on the touch panel 70*a* (hereinafter, referred to as "Touch-Down").

A state in which a finger or a stylus is in touch with the touch panel 70*a* (hereinafter, referred to as "Touch-On").

An operation of a finger or a stylus moving over the touch panel 70*a* while being in touch with the touch panel 70*a* (hereinafter, referred to as "Touch-Move").

The detachment (release) of a finger or a stylus that has been in touch with the touch panel 70*a*, i.e., the end of a touch on the touch panel 70*a* (hereinafter, referred to as "Touch-Up").

A state in which nothing touches the touch panel 70*a* (hereinafter, referred to as "Touch-Off").

When the Touch-Down is detected, the Touch-On is simultaneously detected. After the Touch-Down, normally, the Touch-On continues to be detected until the Touch-Up is detected. The Touch-On is simultaneously detected also in a case where the Touch-Move is detected. Even when the Touch-On is detected, the Touch-Move is not detected unless a touch position moves. After the Touch-Up of all the fingers or styluses that have been in touch is detected, the Touch-Off is detected.

These operations and states and a position coordinate on the touch panel 70*a* at which a finger or a stylus is in touch are notified to the system control unit 50 via an internal bus. Based on the notified information, the system control unit 50 then determines the type of an operation (touch operation) performed on the touch panel 70*a*. In the Touch-Move, a moving direction of a finger or a stylus moving on the touch panel 70*a* can also be determined for each perpendicular component/horizontal component on the touch panel 70*a*, based on a change in position coordinate. In a case where it is detected that the Touch-Move is performed for a predetermined distance or more, the system control unit 50 determines that a slide operation has been performed. An operation of swiftly moving a finger by a certain amount of distance with the finger being in touch with the touch panel 70*a* and then detaching the finger will be referred to as a flick. In other words, the flick is an operation of swiftly moving the finger over the touch panel 70*a* like a flip. In a case where it is detected that the Touch-Move has been performed at a predetermined speed or more for a predetermined distance or more, and the Touch-Up is detected in this state, the system control unit 50 determines that a flick has been performed (it can be determined that a flick has been performed subsequent to the slide operation). Furthermore, a touch operation of touching a plurality of locations (e.g. two points) together (multi-touch), and bringing the touch positions closer to each other will be referred to as "pinch-in", and a touch operation of bringing the touch positions away from each other will be referred to as "pinch-out". The pinch-out and the pinch-in will be collectively referred to as a pinch operation (or simply "pinch"). As the touch panel 70*a*, a touch panel of any of the following various types can be used: a resistive touch panel, a capacitive touch panel, a surface acoustic wave touch panel, an infrared touch panel, an electromagnetic induction type touch panel, an image recognition type touch panel, and an optical sensor type touch panel. Some touch panels detect a touch upon detecting contact with the touch panel 70*a* while the other touch panels detect a touch upon detecting the proximity of a finger or a stylus to the touch panel 70*a*. A touch panel of any types can be used.

Next, a basic operation of an imaging apparatus (the digital camera) 100 according to the present example embodiment will be described.

As described below, the imaging apparatus 100 (the system control unit 50) switches an image capturing mode of the imaging apparatus between a medical mode (e.g. medical mode is set to ON) and a normal image capturing mode (e.g. medical mode is set to OFF). For example, the imaging apparatus 100 can switch between ON and OFF of a medical mode by a setting on a menu screen. In a case where ON/OFF of the medical mode is switched, an operation to be described below becomes effective in a case where the medical mode is set to ON. In a case where the medical mode is set to OFF, a mode becomes a normal image capturing mode. While, in the present example embodiment, a mode is switched between the medical mode and the normal image capturing mode by an operation on the menu screen, switching between the medical mode and the normal image capturing mode can be performed in accordance with an operation on a specific operation member. More details of switching to a medical mode are given below with reference to FIG. 14. A medical mode may be a mode of the imaging apparatus for use in a medical workplace or medical environment, in which the imaging apparatus may perform various operations for use in carrying out a medical process.

Operations in the medical mode can include one or more of patient information acquisition processing, user information acquisition processing, region information acquisition processing, affected area image capturing processing, affected area image confirmation processing, and affected area image retransmission processing.

In the patient information acquisition processing, the imaging apparatus 100 transmits image data, such as a barcode or a two-dimensional code, of a patient ID that has been read or acquired as a LV image, to the in-hospital system 1502 via the communication unit 54. Then, the imaging apparatus 100 receives and acquires patient information, such as a name, gender, and age, that is based on the code included in the image data, from the in-hospital system 1502 via the communication unit 54. Data to be transmitted to the in-hospital system 1502 can be acquired in the following manner. More specifically, a code is acquired from image data in the imaging apparatus 100, code information is transmitted to the in-hospital system 1502, and patient information is acquired from the in-hospital system 1502 based on the code. Alternatively, the imaging apparatus 100 can acquire an ID code from an integrated circuit (IC) chip embedded in a patient's registration card, and acquire patient information corresponding to the ID code, from the in-hospital system 1502.

In the user information acquisition processing, the imaging apparatus 100 transmits, to the in-hospital system 1502 via the communication unit 54, image data obtained by reading an ID code (barcode, two-dimensional code, etc.) of a user (doctor, nurse) of a medical image or image data obtained as a captured LV image of the ID code. Then, the imaging apparatus 100 receives and acquires user information, such as a name and a medical diagnosis and a hospital department of a user (doctor/nurse, etc.), obtained based on the code included in the image data from the in-hospital system 1502 via the communication unit 54. Data to be transmitted to the in-hospital system 1502 can be acquired in the following manner. More specifically, a code is acquired from image data in the imaging apparatus 100, code information is transmitted to the in-hospital system 1502, and user information is acquired from the in-hospital system 1502 based on the code.

In the region information acquisition processing, the imaging apparatus 100 acquires list information of regions from the in-hospital system 1502 via the communication unit 54, and the user selects a region corresponding to an affected area from the region list and determines the region. For example, the imaging apparatus 100 may determine region information based on the selected region. The region information may be information associated with an area or region of a subject (e.g. a patient), such as, a face, neck arm, or leg region or any other region of a subject's body. For example, the region information may include information identifying the selected region (e.g. region name).

In the affected area image capturing processing, the imaging apparatus 100 captures an image of a subject (affected area of patient) by an image capturing operation of the user, records obtained image data into the recording medium 200 in association with medical information including, patient information, user information, and region information, and transmits the image data to the in-hospital system 1502 via the communication unit 54. As a method of associating image data and medical information, medical information can be embedded into a part of image data. Alternatively, image data and medical information can be stored as separated files while the files are associated with each other using file names.

In the affected area image confirmation processing, a thumbnail image captured in the affected area image capturing processing and medical information associated with image data are displayed, and the user executes processing of confirming the thumbnail image and the medical information. A result of the confirmation, including OK or not OK, is transmitted to the in-hospital system 1502.

In the affected area image retransmission processing, processing of retransmitting image data that has been generated in the affected area image capturing processing but failed to be properly transmitted to the in-hospital system is executed. The causes of the transmission failure include an error in communication between the imaging apparatus 100 and the in-hospital system 1502 and an error in communication between the in-hospital system 1502 and a database.

<Processing of Switching to Medical Mode>

Figure 14:
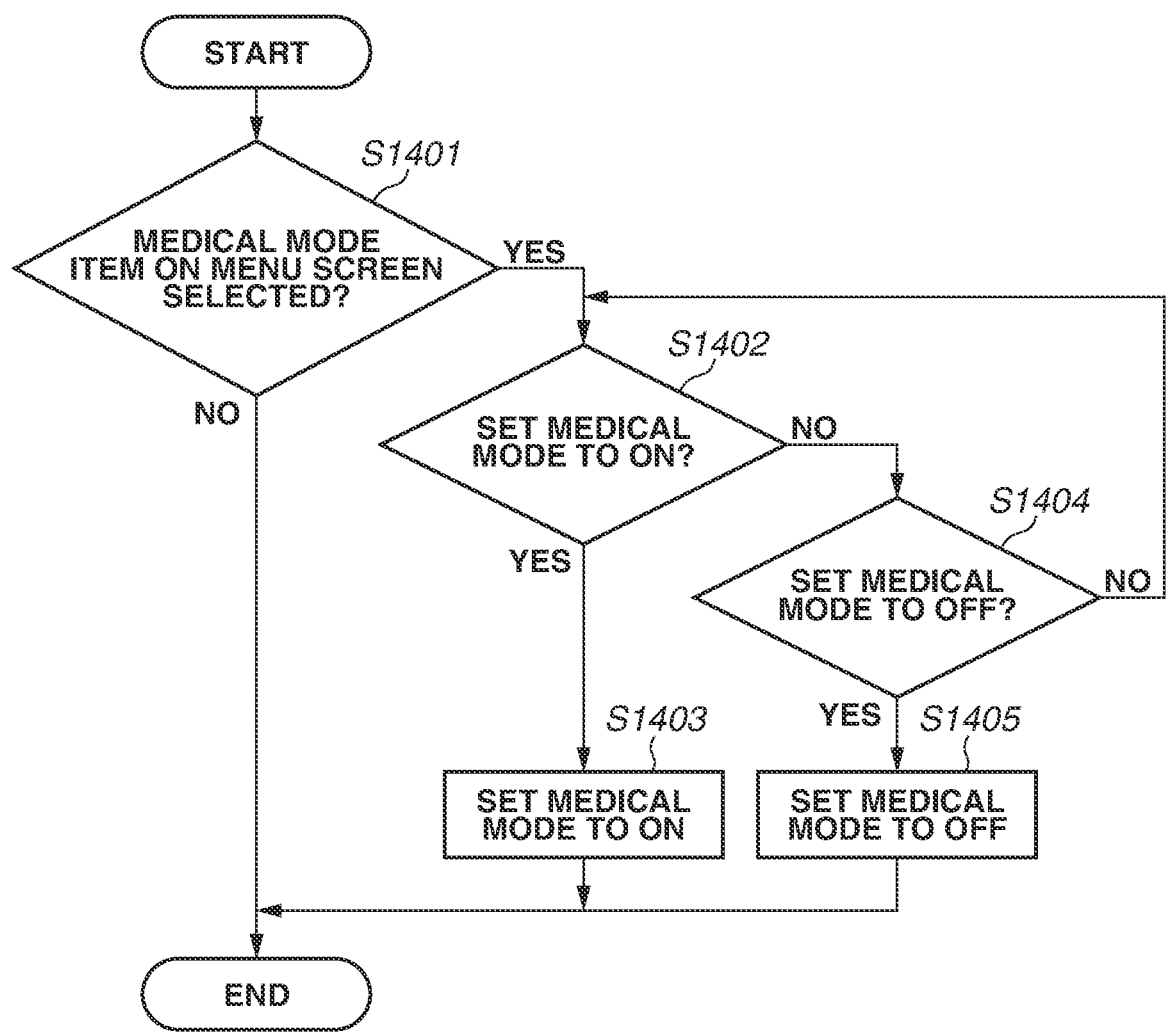
FIG. 14 is a flowchart of medical mode switching processing.

Hereinafter, processing of implementing an operation of switching between ON and OFF of the medical mode will be described with reference to FIG. 14. FIG. 14 is a flowchart illustrating an example of a procedure of switching between ON and OFF of the medical mode according to an example embodiment of the present invention. Irrespective of whether the medical mode is set to ON or OFF, the processing of the flowchart is started by the user pressing the MENU button 81 of the operation members. Nevertheless, during the patient information acquisition processing, the user information acquisition processing, the region information acquisition processing, the affected area image capturing processing, the affected area image confirmation processing, or the affected area image retransmission processing, the start of the processing of the flowchart is disabled even when the user presses the MENU button. Each piece of processing in FIG. 14 is implemented by the system control unit 50 loading a program stored in the nonvolatile memory 56 into the system memory 52 and executing the program.

In step S1401, the system control unit 50 determines whether the user has selected a medical mode item on a MENU screen. The selection is performed by a touching operation on a medical mode item or a pressing operation on the SET button 75 in a state in which a selection frame is set on a medical mode frame by a dial operation or a cross key operation. In a case where the medical mode item is selected (YES in step S1401), the processing proceeds to step S1402. In a case where the medical mode item is selected (NO in step S1401), the processing is ended.

In step S1402, the system control unit 50 displays ON and OFF as sub items and determines whether the user has selected the ON item. The selection is performed by a touching operation on the ON item or a pressing operation on the SET button 75 in a state in which a selection frame is set on the ON item by a dial operation or a cross key operation. In a case where the ON item is selected (YES in step S1402), the processing proceeds to step S1403. In a case where the ON item is not selected (NO in step S1402), the processing proceeds to step S1404.

In step S1403, the system control unit 50 sets the medical mode to ON.

In step S1404, the system control unit 50 determines whether the user has selected the OFF item. The selection is performed by a touching operation on the OFF item or a pressing operation on the SET button 75 in a state in which a selection frame is set on the OFF item by a dial operation or a cross key operation. In a case where the OFF item is selected (YES in step S1404), the processing proceeds to step S1405. In a case where the OFF item is not selected (NO in step S1404), the processing returns to step S1402.

In step S1405, the system control unit 50 sets the medical mode to OFF. In other words, the imaging apparatus 100 operates in the normal image capturing mode without operating in the medical mode. In the normal image capturing mode, the imaging apparatus 100 performs exposure control and ranging control on a subject in accordance with the first shutter switch signal SW1 being turned ON as described above. Then, the imaging apparatus 100 executes an operation as a digital camera in the normal image capturing mode. More specifically, the imaging apparatus 100 executes the operation of capturing an image in accordance with the second shutter switch signal SW2 being turned ON and recording the captured image into the recording medium 200 as a still image file.

<Live View Screen Display>

Figure 3A:
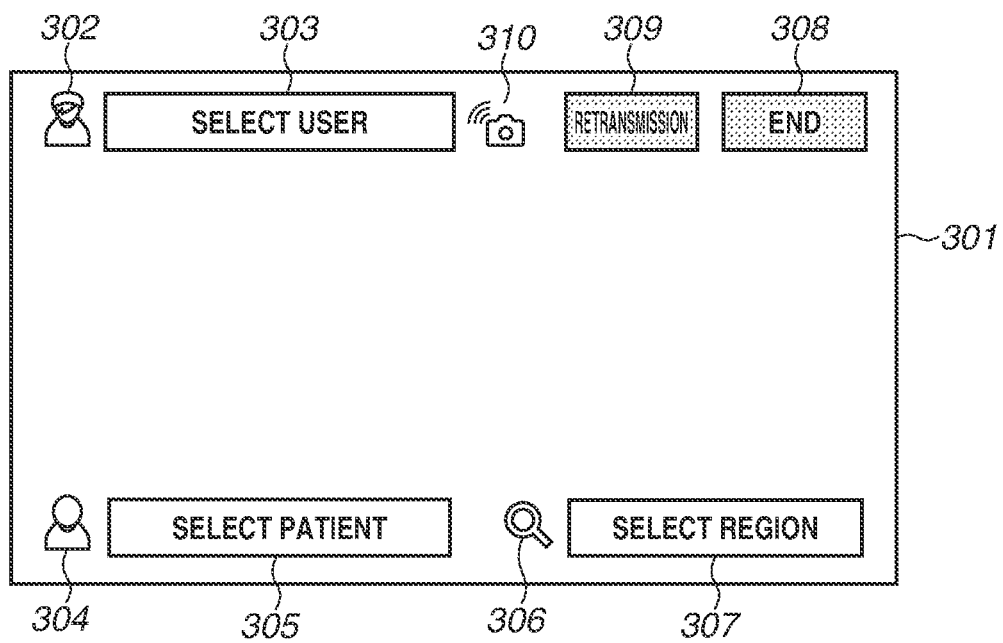
FIGS. 3A and 3B are diagrams each illustrating an example of a live view screen that is displayed in a medical mode.
Figure 3B:
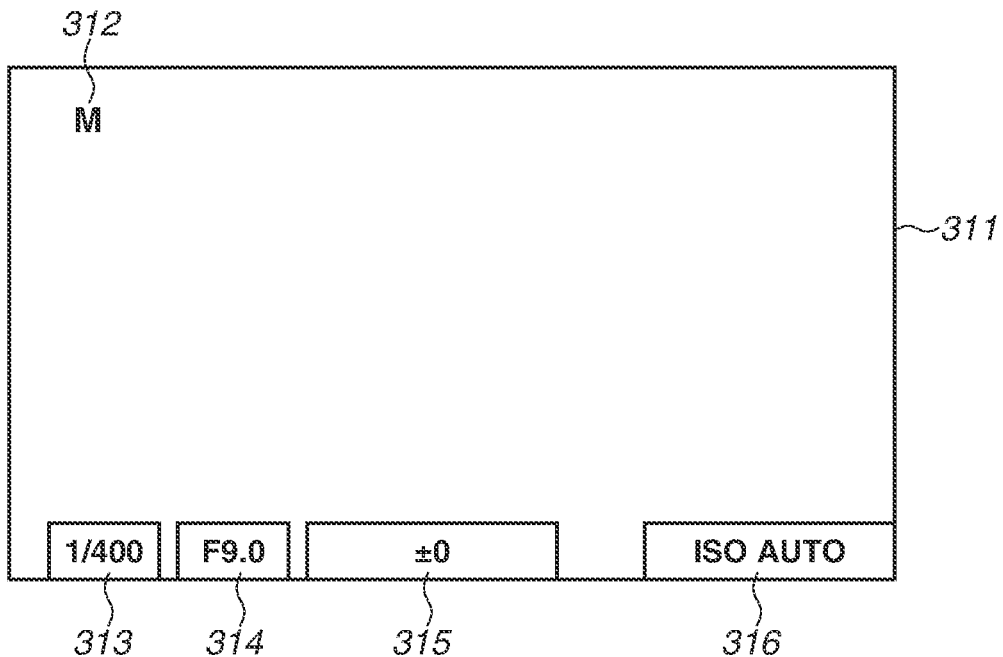

FIGS. 3A and 3B each illustrate an example of a live view screen that is displayed on the display unit 28 according to the present example embodiment when the digital camera 100 is in an imaging standby state while the medical mode is set to ON.

A LV display setting includes medical information display and imaging parameter display. By the user pressing the display switching button 83, the LV display setting can be switched between the medical information display and the imaging parameter display (e.g. the display switching button 83 is an example of a specific operation member to which display switching is allocated).

FIG. 3A illustrates an example of a live view screen that is displayed when the LV display setting is set to the medical information display (e.g. a first display).

A live view image captured by the imaging unit 22 is displayed in an area 301. On the live view image, icons 302, 304, 306, and 310, text boxes (display frames) 303, 305, and 307, and buttons 308 and 309 are superimposed and displayed.

The icon 302 indicates a user and shows that information in the text box 303 next to the icon 302 is about the user. After user information is acquired in the user information acquisition processing in step S410, the icon 302 can be changed to an icon based on the acquired user information.

The text box 303 is a display frame for user information display. By a touching operation on the text box 303 for user information or a pressing operation on the SET button 75 after a selection frame (cursor) is moved to the text box 303 for user information by a dial operation or a cross key operation, the processing transitions to the user information acquisition processing in step S410. In a case where user information is not set, a message "select user" as illustrated in FIG. 3A is displayed to notify that a user is unset. After user information is acquired in the user information acquisition processing in step S410, user information (user name) is displayed in the text box 303 for user information.

The icon 304 indicates a patient and shows that information in the text box 305 next to the icon 304 is about the patient. After patient information is acquired in the patient information acquisition processing in step S408, the icon 304 can be changed to an icon based on the acquired patient information. As an example, the icon 304 can be changed to an icon based on the gender or age of the patient.

The text box 305 is a display frame for patient information display. By a touching operation on the text box 305 for patient information or a pressing operation on the SET button 75 after a selection frame (cursor) is moved to the text box 305 for patient information by a dial operation or a cross key operation, the processing transitions to the patient information acquisition processing in step S408. In a case where patient information is not set, a message "select patient" as illustrated in FIG. 3A is displayed to notify that a patient is unset. After patient information is acquired in the patient information acquisition processing in step S408, the acquired patient information (patient name) is displayed in the text box 305 for patient information. Because patient information is important information that must not be mistaken, not only a patient name but also gender and age can be displayed.

The icon 306 indicates a region and shows that information in the text box 307 next to the icon 306 is about selection of the region. After region information is acquired in the region information acquisition processing in step S412, the icon 306 can be switched to an icon based on the acquired region information.

The text box 307 is a display frame for region information display. By a touching operation on the text box 307 for region information or a pressing operation on the SET button 75 after a selection frame (cursor) is moved to the text box 307 for region information by a dial operation or a cross key operation, the processing transitions to the region information acquisition processing in step S412. In a case where region information is not set, a message "select region" as illustrated in FIG. 3A is displayed to notify that a region is unset. After region information is acquired in the region information acquisition processing in step S412, the acquired region information (region name) is displayed in the text box 307 for region information.

When the user fully presses the shutter button 61 during display of the live view screen, the processing transitions to the affected area image capturing processing in step S425. In the affected area image capturing processing in step S425, image capturing is performed, and the obtained image data is recorded in association with medical information which may include one or more of user information, patient information, and region information displayed in the text boxes 303, 305, and 307, respectively, and the image data is transmitted to the in-hospital system 1502.

The button 308 is an end button. When the user ends the capturing of a necessary number of images of an affected area of a patient, the user presses the button 308. A pressing operation on the button 308 transitions the processing to the affected area image confirmation processing in step S427, and then when the user selects an OK button or a cancel button, a result of the selection is transmitted to the in-hospital system 1502. The pressing operation on the button 308 can clear the settings of the text box 303 for user information, the text box 305 for patient information, and the text box 307 for region information.

A button 309 is a retransmission button. A touching operation on the button 309 for retransmission on the screen or a pressing operation on the SET button 75 after a selection frame is moved to the button 309 for retransmission by a dial operation transitions the processing to the affected area image retransmission processing in step S429. In the affected area image retransmission processing in step S429, retransmission of image data that has failed to be transmitted to the in-hospital system 1502 even though the user selects an OK button in the affected area image confirmation processing in step S427 is performed.

The icon 310 is an icon indicating a communication state. The icon 310 displays whether the imaging apparatus 100 has not been connected with the in-hospital system 1502 (server 1501) or has been connected with the in-hospital system 1502 (server 1501).

FIG. 3B illustrates an example of a live view screen that is displayed when the LV display setting is set to imaging parameter display (e.g. a second display). A live view image of a subject is displayed in an area 311. In a case where the LV display setting is set to the imaging parameter display, the following information regarding an image capturing setting is displayed together with a live view image (live image). An icon 312 is an image capturing mode icon indicating an image capturing mode. An item 313 indicates a setting value of a shutter speed. An item 314 indicates an aperture value. An item 315 indicates an exposure compensation value. An item 316 indicates an ISO value.

In the above-described manner, in a case where the LV display setting is set to the imaging parameter display, currently-set various imaging parameters (the setting of an image capturing mode and setting values of various imaging parameters, such as in-focus region (e.g. AF frame), shutter speed, and an aperture value) are displayed. In the imaging parameter display, the button 308 for an end of image capturing, the button 309 for retransmission, and the icon 310 indicating the communication state that are displayed when the LV display setting is set to the medical information display can also be displayed in the medical mode.

<Processing in Medical Mode>

Figure 4A:
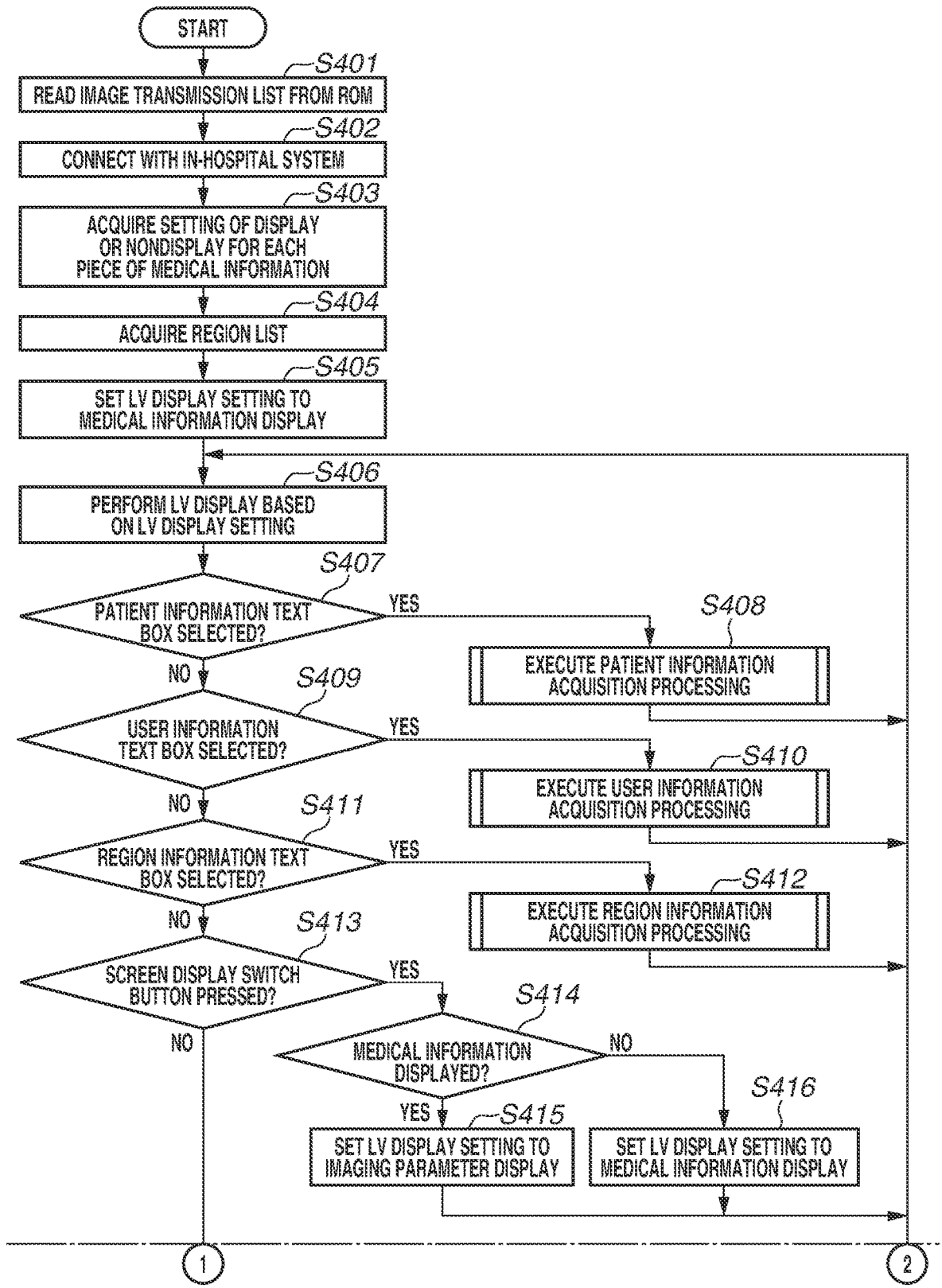
FIGS. 4A and 4B are flowcharts illustrating processing that is executed in the medical mode.
Figure 4B:
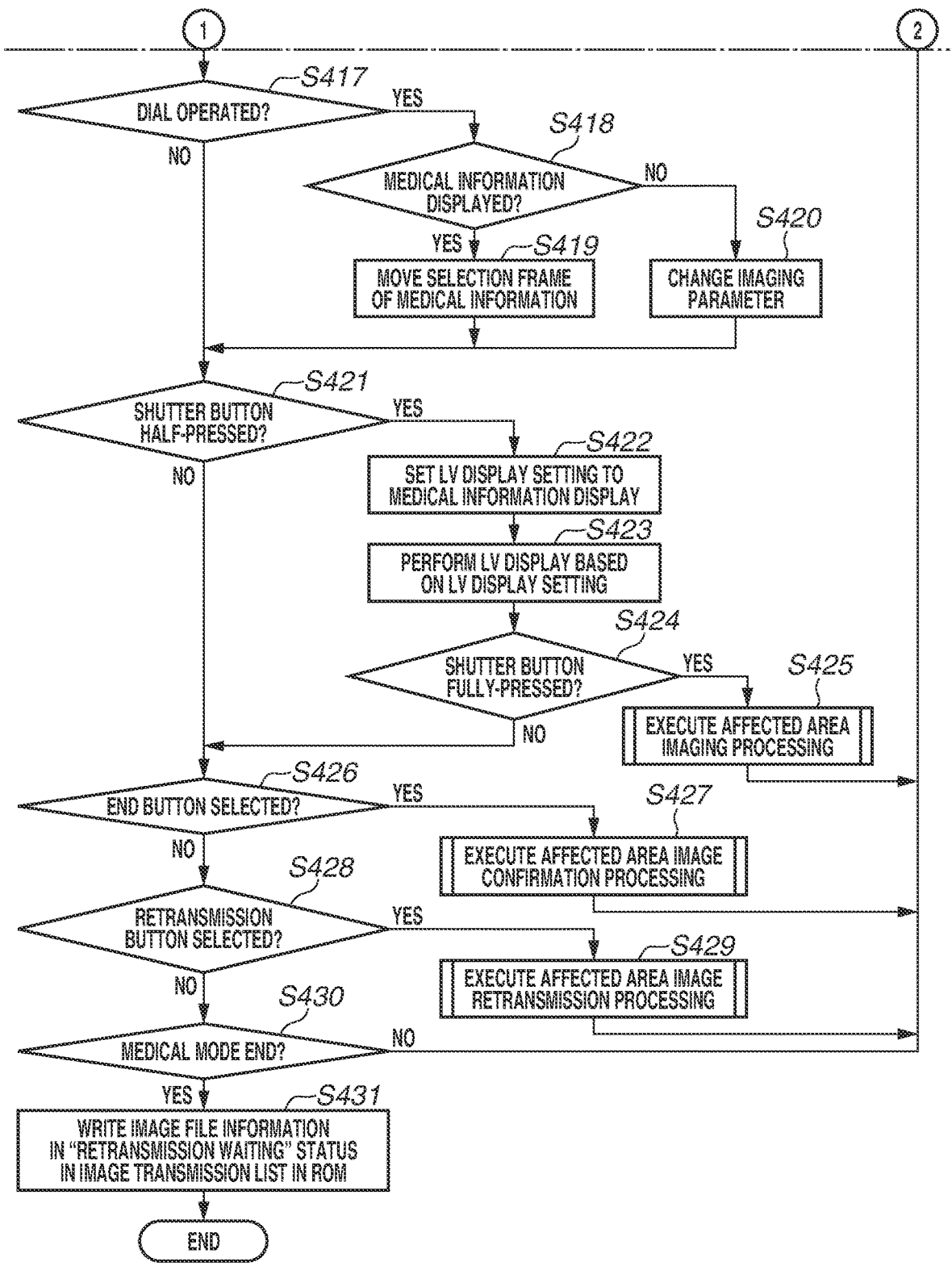

Hereinafter, the processing that is executed by the imaging apparatus 100 in the medical mode according to an example embodiment of the present invention will be described with reference to FIGS. 4A and 4B. FIGS. 4A and 4B are diagrams of a flowchart illustrating processing that is executed by the imaging apparatus 100 from a start to an end of the medical mode. The medical mode is started by the user turning the power ON in a state in which the medical mode is set to ON or the user switching the setting of the medical mode from OFF to ON. Each piece of processing in FIGS. 4A and 4B is implemented by the system control unit 50 loading a program stored in the nonvolatile memory 56 into the system memory 52 and executing the program when the power switch 72 is turned on. Each piece of processing in FIG. 6, 8, 9, 11A and 11B, and 13, which indicate sub procedures of the flowchart illustrated in FIGS. 4A and 4B, is implemented by the system control unit 50 loading a program stored in the nonvolatile memory 56 into the system memory 52 and executing the program.

In step S401, the system control unit 50 reads an image transmission list from the nonvolatile memory 56. The image transmission list is to be used to retransmit unsent image data in the affected area image retransmission processing in step S429 if any image data has failed to be transmitted when the imaging apparatus 100 has operated in the medical mode the last time.

In step S402, the system control unit 50 connects with the in-hospital system 1502 via the communication unit 54. In the present example embodiment, the system control unit 50 wirelessly connects to the in-hospital system 1502 via the server 1501 as illustrated in FIG. 15, but the system control unit 50 can connect to the in-hospital system 1502 via a cable.

In step S403, the system control unit 50 acquires a setting of display or nondisplay for each piece of medical information (user information, patient information, region information) from the in-hospital system 1502. The setting is to be used to switch between display and nondisplay of medical information indicated by the icons 302, 304, and 306 and text boxes 303, 305, and 307.

In step S404, the system control unit 50 acquires, from the in-hospital, a list of regions to be selected by the user in the system region information acquisition processing.

In step S405, the system control unit 50 sets the LV display setting to medical information display. This is because the medical information display as illustrated in FIG. 3A is performed in a default state of the medical mode. For this reason, in a case where the power is turned on when the medical mode is set to ON or when the mode is switched to the medical mode, the live view screen is initially displayed in the medical information display as illustrated in FIG. 3A.

In step S406, when the LV display setting is set to the medical information display, the system control unit 50 displays medical information (patient information, user, region information) as illustrated in FIG. 3A, and when the LV display setting is set to the imaging parameter display, the system control unit 50 displays specific imaging parameters as illustrated in FIG. 3B.

In step S407, the system control unit 50 determines whether the user has selected the text box 305 for patient information on the screen. The selection is performed by either of a touching operation on the text box 305 or a pressing operation on the SET button 75 in a state in which a selection frame is set on the text box 305 for patient information by a dial operation or a cross key operation to be described below. The dial operation is an operation on the main electronic dial 71 or the sub electronic dial 73, and the cross key operation is an operation on the four directional key 74. In a case where the text box 305 for patient information has been selected (YES in step S407), the processing proceeds to step S408. In a case where the text box 305 for patient information has not been selected (NO in step S407), the processing proceeds to step S409.

In step S408, the system control unit 50 executes the patient information acquisition processing to receive patient information from the in-hospital system 1502 by transmitting, to the in-hospital system 1502, a barcode image of a patient whose image has been captured by the imaging unit 22. The patient information to be acquired from the in-hospital system 1502 includes a patient name, a patient ID, age, and gender. Alternatively, as another configuration, the system control unit 50 can analyze a captured barcode image, transmit analyzed barcode information to the in-hospital system 1502, and receive patient information from the in-hospital system 1502. The patient information acquisition processing will be described in detail below.

In step S409, the system control unit 50 determines whether the user has selected the text box 303 for user information on the screen. The selection is performed by either of a touching operation on the text box 303 or a pressing operation on the SET button 75 in a state in which a selection frame is set on the text box 303 for user information by a dial operation or a cross key operation. In a case where the text box 303 for user information has been selected (YES in step S409), the processing proceeds to step S410. In a case where the text box 303 for user information has not been selected (NO in step S409), the processing proceeds to step S411.

In step S410, the system control unit 50 executes the user information acquisition processing to receive user information from the in-hospital system 1502 by transmitting a barcode image of a user (doctor or nurse) to the in-hospital system 1502. The user information includes a user name, a user ID, and a name of a department to which the user belongs. Alternatively, as another configuration, the system control unit 50 can analyze a captured barcode image, transmit analyzed barcode information to the in-hospital system 1502, and receive user information from the in-hospital system 1502. The user information acquisition processing will be described in detail below.

In step S411, the system control unit 50 determines whether the user has selected the text box 307 for region information on the screen. The selection is performed by a pressing operation on the text box 307 or a pressing operation on the SET button 75 in a state in which a selection frame is set on the text box 307 for region information by a dial operation or a cross key operation. In a case where the text box 307 for region information has been selected (YES in step S411), the processing proceeds to step S412. In a case where the text box 307 for region information has not been selected (NO in step S411), the processing proceeds to step S413.

In step S412, the system control unit 50 displays the region list acquired in step S404 and prompts the user to select a region from the region list, to execute the region information acquisition processing to determine region information. The region information acquisition processing will be described in detail below.

The processing in steps S407 to S412 is executed in a case where the LV display setting is set to the medical information display in which the text box 303 for user information, the text box 305 for patient information, and the text box 307 for region information are displayed. In a case where the LV display setting is set to the imaging parameter display, because the text box 303 for user information, the text box 305 for patient information, and the text box 307 for region information are not displayed, the processing in steps S407 to S412 is not executed. In other words, while medical information can be changed in accordance with a user operation in a case where the LV display setting is set to the medical information display, medical information cannot be changed in accordance with a user operation in a case where the LV display setting is set to the imaging parameter display.

In step S413, the system control unit 50 determines whether the user has pressed the display switching button 83. In a case where the user has pressed the display switching button 83 (YES in step S413), the processing proceeds to step S414. In a case where the user has not pressed the display switching button 83 (NO in step S413), the processing proceeds to step S417.

In step S414, the system control unit 50 determines whether the LV display setting is set to the medical information display. In a case where the LV display setting is set to the medical information display (YES in step S414), the processing proceeds to step S415. In a case where the LV display setting is not set to the medical information display (NO in step S414), the processing proceeds to step S416.

In step S415, the system control unit 50 sets the LV display setting to the imaging parameter display, and then the processing returns to step S406. In this case, because the LV display setting is changed from the medical information display to the imaging parameter display, in step S406, LV display is changed to the display including imaging parameter information together with a live view image as illustrated in FIG. 3B.

In step S416, the system control unit 50 sets the LV display setting to the medical information display, and then the processing returns to step S406. In this case, because the LV display setting is changed from the imaging parameter display to the medical information display, in step S406, LV display is changed to the display including medical information together with a live view image as illustrated in FIG. 3A. In step S417, the system control unit 50 determines whether the user has performed a dial operation on the main electronic dial 71 or the sub electronic dial 73. In a case where the user has performed a dial operation (YES in step S417), the processing proceeds to step S418. In a case where the user has not performed a dial operation (NO in step S417), the processing proceeds to step S421.

In step S418, the system control unit 50 determines whether the LV display setting is set to the medical information display. In a case where the LV display setting is set to the medical information display (YES in step S418), the processing proceeds to step S419. In a case where the LV display setting is not set to the medical information display (NO in step S418), the processing proceeds to step S420.

In step S419, the system control unit 50 moves a selection frame for medical information. The selection frame for medical information is displayed on either one of the text box 303 for user information, the text box 305 for patient information, and the text box 307 for region information, and moves in the order of the text box 303 for user information, the text box 305 for patient information, and the text box 307 for region information. Next to the text box 307 for region information, the selection frame moves to the text box 303 for user information. In a case where the selection frame moving operation is performed during a half press operation on the shutter button 61, the movement of the selection frame of medical information can be enabled. During the medical information display, not only by a dial operation, the selection frame for medical information can also be moved by a cross key operation similarly to a dial operation.

In step S420, the system control unit 50 changes imaging parameters. As an example, the imaging parameters may include one or more of a shutter speed, an aperture value, an exposure compensation value, in-focus region and an ISO value. For each image capturing mode, the imaging parameters are individually allocated to the main electronic dial 71 and the sub electronic dial 73. For example, in a case where the image capturing mode is a Tv mode, a setting value of a shutter speed is changed in accordance with an operation on the main electronic dial 71, and in a case where the image capturing mode is an Av mode, a setting value of an aperture value is changed in accordance with an operation on the main electronic dial 71.

In the above-described manner, during the medical information display, the selection frame of medical information is moved in accordance with a dial operation, and during the imaging parameter display, a setting value of an imaging parameter for each of the image capturing modes allocated to the dials 71 and 73 is changed in accordance with a dial operation. In a case where a function of an imaging parameter change is allocated to a different operation member, such as the touch bar 82, an imaging parameter can be made changeable irrespective of the LV display setting. In this case, even in a case where the LV setting is set to the medical information display, an imaging parameter can be changed in accordance with a user operation. Thus, one or more imaging parameters displayed, during the medical information display or the imaging parameter display, may be changed via user operation including dial operation, operation of a touch bar, or any other of similar user operations.

In step S421, the system control unit 50 determines whether the user has half pressed the shutter button 61 (i.e., the first shutter switch signal SW1 has been output). In a case where the user has half pressed the shutter button 61 (YES in step S421), the processing proceeds to step S422. In a case where the user has not half pressed the shutter button 61 (NO in step S421), the processing proceeds to step S426.

In step S422, the system control unit 50 sets the LV display setting to the medical information display. Also in the medical mode, similarly to the normal image capturing mode, an imaging preparation operation is executed in accordance with a half-press operation of the shutter button 61.

Because the LV display setting has been changed to the medical information display in step S422, in step S423, the system control unit 50 changes the display to the medical information display as illustrated in FIG. 3A.

In a case where medical information, such as patient information, is to be stored in an imaging apparatus in association with image data, it is important for the user to confirm that the medical information is correct medical information, and the user desires to confirm the medical information at the time of image capturing. Furthermore, to capture a high-quality image and obtain high-quality image data, it is also important to confirm imaging parameters relating to image capturing (Av/Tv/exposure compensation value/Iso, etc.) at the time of image capturing. In view of the foregoing, in the imaging apparatus 100 according to the present example embodiment, in a case where the shutter button 61 has been half pressed, even if the LV display setting is set to the imaging parameter display setting, the imaging parameter display is switched to the medical information display and live view display is performed. Accordingly, a user can confirm medical information before image capturing, whereby an inputting error of medical information can be prevented. In the present example embodiment, the LV display setting is changed to the medical information display in accordance with the half press of the shutter button 61. Alternatively, the setting of the LV display setting can be configured to be temporarily changed to the medical information display while the shutter button 61 is being half pressed. In this case, in accordance with the detachment of a finger from the shutter button 61, the display returns to the display based on the LV display setting set before the shutter button 61 is half pressed.

In step S424, the system control unit 50 determines whether the user has fully pressed the shutter button 61.

More specifically, the system control unit 50 determines whether the second shutter switch signal SW2 has been output. In a case where the user has fully pressed the shutter button 61 (YES in step S424), the processing proceeds to step S425. In a case where the user has not fully pressed the shutter button 61 (NO in step S424), the processing proceeds to step S426.

In step S425, the system control unit 50 executes the affected area image capturing processing by generating image data by performing image capturing, record medical information (user information, patient information, region information) and the image data in association with each other, and transmitting the image data to the in-hospital system 1502. The affected area image capturing processing will be described in detail below. Thus, in an example arrangement, after at least the medical information (e.g. one or more of user information, patient information, region information) and a live image have been displayed (during the medical information display e.g. by a half press operation on the shutter button 61), image data may be obtained by imaging unit 22 by performing image capturing in response to a full press operation on the shutter button 61. The obtained image data is then associated with the medical information in response to the full press operation on the shutter button 61. This enables medical information for the live image displayed to be checked before image capturing and association of the image data with the medical information. In an example, when display is switched to the imaging parameter display, imaging parameters relating to the live image displayed can be checked before image capturing.

In step S426, the system control unit 50 determines whether the user has selected the button 308 to end the processing on the screen. Alternatively, the system control unit 50 can determine whether the user has pressed the SET button 75 in a state in which a selection frame is set on the button 308 by a dial operation or a cross key operation. Alternatively, in a case where the end button function is allocated to a specific operation member, the system control unit 50 can determine whether the user has operated the specific operation member to which the end button function is allocated. In a case where the button 308 has been selected (YES in step S426), the processing proceeds to step S427. In a case where the button 308 has not been selected (NO in step S426), the processing proceeds to step S428.

In step S427, the system control unit 50 executes the affected area image confirmation processing by prompting the user to confirm an affected area image and select either the OK button or the cancel button and transmitting a result of the selection to the in-hospital system 1502 via the communication unit 54. The affected area image confirmation processing will be described in detail below.

In step S428, the system control unit 50 determines whether the user has selected the button 309 for retransmission on the screen. Alternatively, the system control unit 50 can determine whether the user has pressed the SET button 75 in a state in which a selection frame is set on the button 309 for retransmission by a dial operation or a cross key operation. Alternatively, in a case where the retransmission button function is allocated to a specific operation member, the system control unit 50 can determine whether the user has pressed the specific operation member to which the retransmission button function is allocated. In a case where the button 309 for retransmission has been selected (YES in step S428), the processing proceeds to step S429. In a case where the button 309 for retransmission has not been selected (NO in step S428), the processing proceeds to step S430.

In step S429, the system control unit 50 executes the affected area image retransmission processing by determining an image that has failed to be transmitted in step S425, from among images in the image transmission list for which the OK button has been selected in the affected area image confirmation processing in step S427 and retransmitting the determined image to the in-hospital system 1502 via the communication unit 54. The affected area image retransmission processing will be described in detail below.

In step S430, the system control unit 50 determines whether the user has ended the medical mode by switching the medical mode to OFF or turning the power OFF. In a case where the user has ended the medical mode (YES in step S430), the processing proceeds to step S431. In a case where the user has not ended the medical mode (NO in step S430), the processing returns to step S406.

In step S431, the system control unit 50 writes, in the nonvolatile memory 56, image file information in a "retransmission waiting" status in the image transmission list. In a case where the power is turned OFF, it is desirable that a current mode (medical mode/normal image capturing mode) is also written into the nonvolatile memory 56, and when the power is turned ON next time, an operation is started in the mode set when the power is turned OFF.

<Patient Information Acquisition Processing/User Information Acquisition Processing>

Figure 5A:
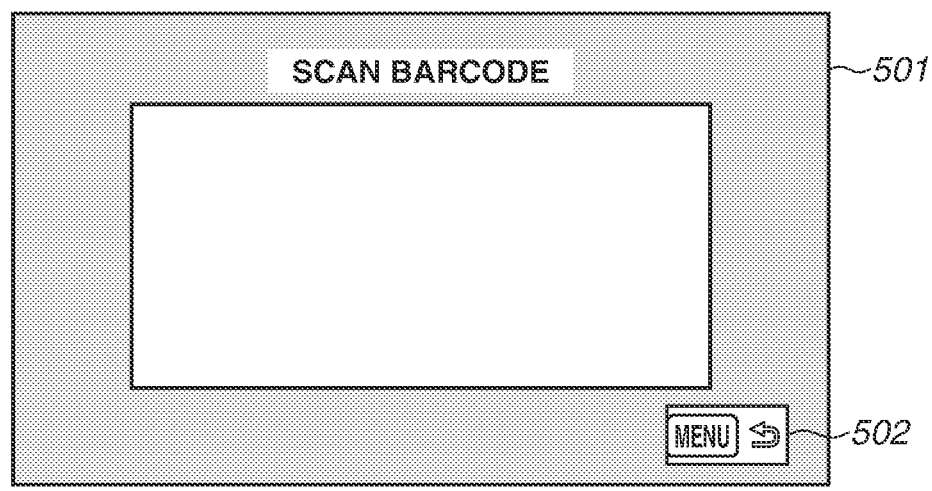
FIGS. 5A to 5C are diagrams each illustrating an example of a screen that is displayed in patient information acquisition processing or user information acquisition processing.
Figure 5B:
Figure 5C:
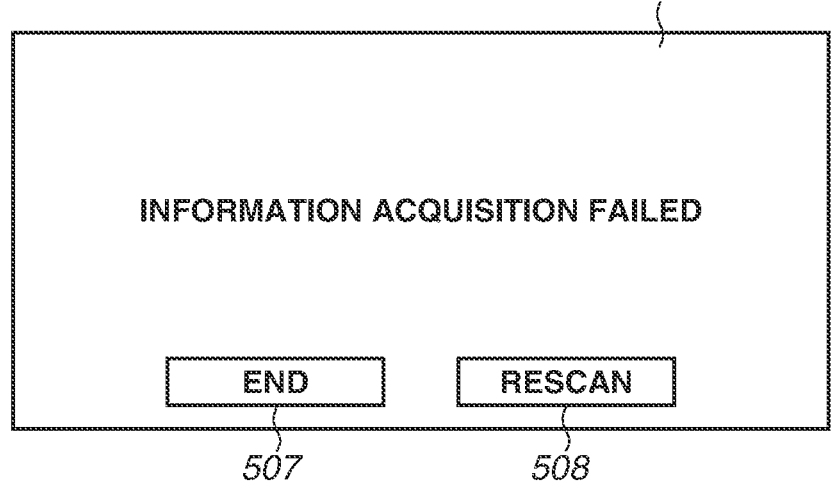

FIGS. 5A to 5C illustrate examples of screens that are displayed in the patient information acquisition processing in step S408 and the user information acquisition processing in step S410, according to the present example embodiment.

FIG. 5A illustrates an example of a barcode acquisition screen.

A live view image is displayed in an area 501. As illustrated in FIG. 5A, a frame of a region to capture a barcode image and a message "SCAN BARCODE" to prompt the user to perform barcode image capturing can be displayed together with the live view image.

A MENU button 502 is a button to close the barcode acquisition screen and also notifies that pressing of the MENU button 502 can close the barcode acquisition screen.

FIG. 5B illustrates an example of an information confirmation screen to prompt the user to confirm information received in step S605 to be described below.

Received information (either patient information or user information) 503, an OK button 504, and a rescan button 505 are displayed on the information confirmation screen.

The OK button 504 is a button that is used when the user selects OK after confirmation of the received information.

The rescan button 505 is a button that is used when the user selects whether to perform image capturing again.

FIG. 5C illustrates an example of an error screen that is displayed in a case where information has failed to be properly received.

A message 506 notifying the user of an error, an end button 507, and a rescan button 508 are displayed on the error screen. A wording of the message 506 can be changed in accordance with the type of the error.

Figure 6:
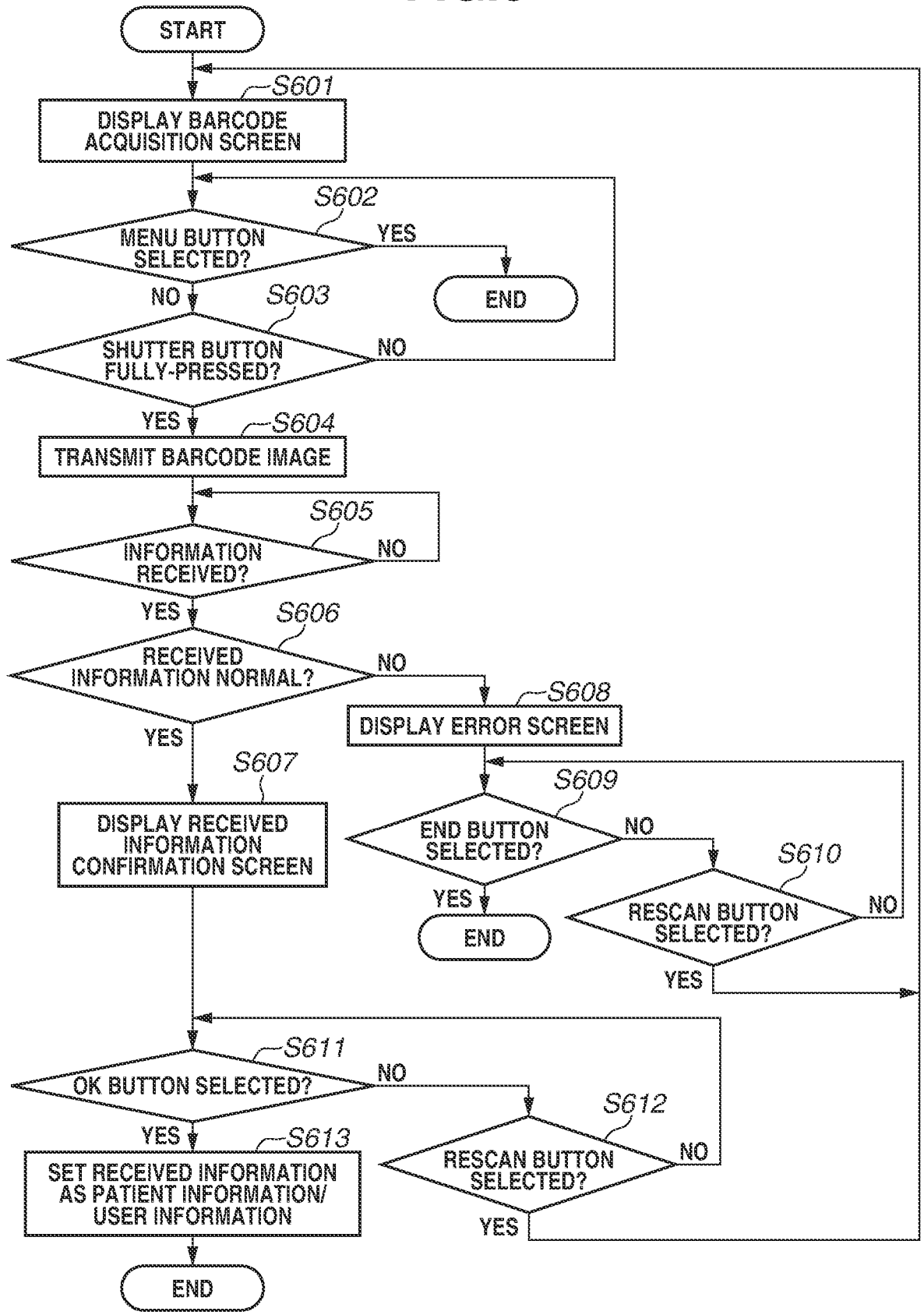
FIG. 6 is a flowchart of the patient information acquisition processing.

Hereinafter, the patient information acquisition processing (step S408) and the user information acquisition processing (step S410) will be described with reference to FIG. 6. Because basic operations in the patient information acquisition processing and the user information acquisition processing are the same, the patient information acquisition processing and the user information acquisition processing will be described with reference to one flowchart.

In step S601, the system control unit 50 displays the barcode acquisition screen as illustrated in FIG. 5A.

In step S602, the system control unit 50 determines whether the user has selected the MENU button 502 on the screen. The selection is performed by a touching operation on the MENU button 502 or a pressing operation on the MENU button 81 of the operation member. In a case where the MENU button has been selected (YES in step S602), the processing ends. In a case where the MENU button has not been selected (NO in step S602), the processing proceeds to step S603.

In step S603, the system control unit 50 determines whether the user has fully pressed the shutter button 61. In a case where the user has fully pressed the shutter button 61 (YES in step S603), the processing proceeds to step S604. In a case where the user has not fully pressed the shutter button 61 (NO in step S603), the processing returns to step S602.

In step S604, the system control unit 50 captures a barcode image using the imaging unit 22 and transmits the captured barcode image to the in-hospital system 1502 via the communication unit 54. The system control unit 50 can acquire a barcode by analyzing a barcode image and transmit barcode information to the in-hospital system via the communication unit 54 without transmitting a barcode image.

In step S605, the system control unit 50 determines whether information has been received from the in-hospital system 1502. In a case where information has been received (YES in step S605), the processing proceeds to step S606. In a case where information has not been received (NO in step S605), the processing in step S605 is executed again.

In step S606, the system control unit 50 determines whether the received information is normal. In a case where the received information is normal (YES in step 5606), the processing proceeds to step S607. In a case where the received information is not normal (NO in step S606), the processing proceeds to step S608.

In step S607, the system control unit 50 displays the information confirmation screen for the received information illustrated in FIG. 5B.

In step S608, the system control unit 50 displays the error screen illustrated in FIG. 5C.

In step S609, the system control unit 50 determines whether the user has selected the end button 507 on the screen The selection is performed by a touching operation on the end button 507 or a pressing operation on the SET button 75 in a state in which a selection frame is set on the end button 507 by a dial operation or a cross key operation. In a case where the end button 507 has been selected (YES in step S609), the processing ends. In a case where the end button has not been selected (NO in step S609), the processing proceeds to step S610.

In step S610, the system control unit 50 determines whether the user has selected the rescan button 508 on the screen. The selection performed by a touching operation on the rescan button 508 or a pressing operation on the SET button 75 in a state in which a selection frame is set on the rescan button 508 by a dial operation or a cross key operation. In a case where the rescan button 508 has been selected (YES in step S610), the processing returns to step S601. In a case where the rescan button 508 has not been selected (NO in step S610), the processing returns to step S609.

In step S611, the system control unit 50 determines whether the user has selected the OK button 504 on the screen. The selection is performed by a touching operation on the OK button 504 or a pressing operation on the SET button 75 in a state in which a selection frame is set on the OK button 504 by a dial operation or a cross key operation. In a case where the OK button 504 has been selected (YES in step S611), the processing proceeds to step S613. In a case where the OK button 504 has not been selected (NO in step S611), the processing proceeds to step S612.

In step S612, the system control unit 50 determines whether the user has selected the rescan button 508 on the screen. The selection is performed by a touching operation on the rescan button 508 or a pressing operation on the SET button 75 in a state in which a selection frame is set on the rescan button 508 by a dial operation or a cross key operation. In a case where the rescan button 508 has been selected (YES in step S612), the processing returns to step S601. In a case where the rescan button 508 has not been selected (NO in step S612), the processing returns to step S611.

In step S613, in a case where the system control unit 50 executes the patient information acquisition processing in step S408, the system control unit 50 sets the information received in step S605 as patient information, and in a case where the system control unit 50 executes the user information acquisition processing in step S410, the system control unit 50 sets the information received in step S605 as user information. As described above, because the patient information acquisition processing and the user information acquisition processing are executed in a case where the LV setting is set to the medical information display, when the processing ends, the screen returns to the medical information display screen illustrated in FIG. 3A. At this time, the information set in the processing is displayed in the text box 305 for patient information or the text box 303 for user information.

<Region Information Acquisition Processing>

Figure 7A:
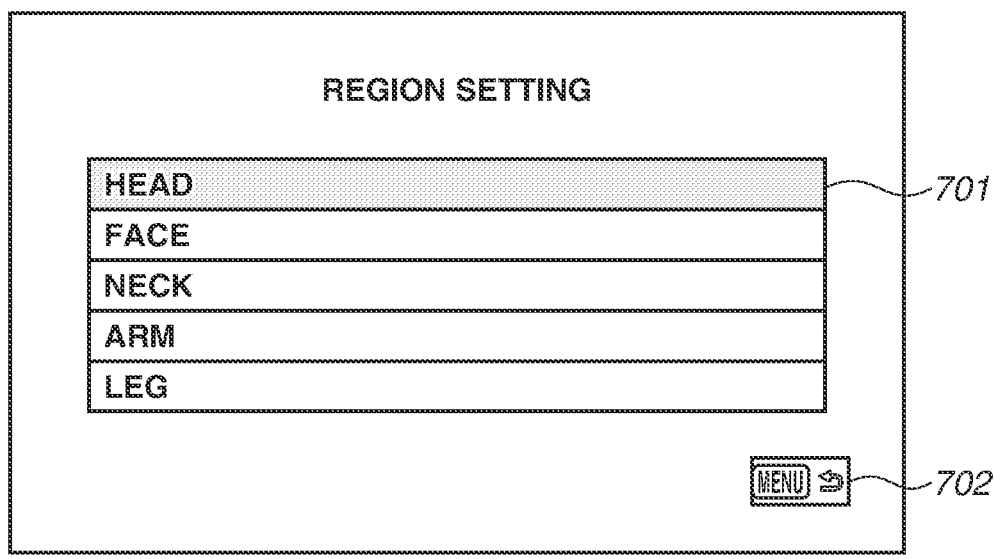
FIGS. 7A and 7B are diagrams each illustrating an example of a screen that is displayed in region information acquisition processing.
Figure 7B:
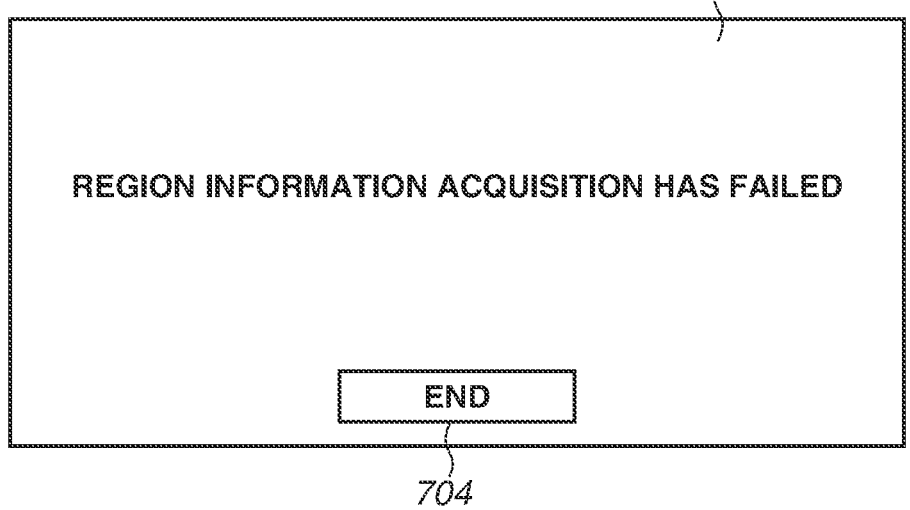

FIGS. 7A to 7B each illustrate an example of a screen that is displayed in the region information acquisition processing (step S412).

FIG. 7A illustrates an example of a region list selection screen.

A region list 701 and a MENU button 702 are displayed on the region list selection screen. The region list 701 may be a display of the region list acquired in step S404. For example, the region list 701 may list one or more areas or regions of a subject (e.g. a patient), such as, a face, neck arm, or leg region or any other region of a subject's body. The MENU button 702 is a button to close the region list selection screen.

FIG. 7B illustrates an example of an error screen.

A message 703 notifying the user of an error and an end button 704 are displayed on the error screen. A wording of the message 703 can be changed in accordance with the type of an error.

Hereinafter, the region information acquisition processing in step S412 will be described with reference to FIG. 8.

In step S801, the system control unit 50 determines whether a region list has been acquired from the in-hospital system 1502 in step S404. In a case where a region list has been acquired (YES in step S801), the processing proceeds to step S802. In a case where a region list has not been acquired (NO in step S801), the processing proceeds to step S803.

In step S802, the system control unit 50 displays the region list selection screen illustrated in FIG. 7A. The region list acquired in step S404 is displayed in the region list 701.

In step S803, the system control unit 50 displays the error screen illustrated in FIG. 7B and ends the processing in accordance with the end button 704 being operated.

In step S804, the system control unit 50 determines whether the user has selected the MENU button 702 on the region list selection screen. The selection is performed by a touch operation on the MENU button 702 or a pressing operation on the MENU button 81 of the operation member. In a case where the MENU button has been selected (YES in step S804), the processing ends. In a case where the MENU button has not been selected (NO in step S804), the processing proceeds to step S805.

In step S805, the system control unit 50 determines whether the user has selected any region in the region list 701 on the region list selection screen. The selection is performed by a touching operation on any region in the region list 701 or a pressing operation on the SET button 75 in a state in which a selection frame is set on any region in the region list by a dial operation or a cross key operation. In a case where a region has been selected (YES in step S805), the processing proceeds to step S806. In a case where a region has not been selected (NO in step S805), the processing returns to step S804.

In step S806, the system control unit 50 sets the region selected by the user in step S805 as region information.

As described above, because the region information acquisition processing is executed in a case where the LV setting is set to the medical information display, when the processing ends, the screen returns to the medical information display screen illustrated in FIG. 3A. At this time, the region information set in the processing is displayed in the text box 307 for region information.

<Affected Area Image Capturing Processing>

Hereinafter, the affected area image capturing processing (step S425) will be described with reference to FIG. 9.

In step S901, the system control unit 50 captures an affected area image using the imaging unit 22 and acquires image data of the affected area image.

In step S902, the system control unit 50 displays the preview of the affected area image captured in step S901. In the preview display, set medical information (patient information, user information, region information) can be displayed in a superimposed manner. The display/nondisplay and a display time of the preview display can be changed in accordance with a user setting.

In step S903, the system control unit 50 stores medical information (patient information, user information, region information) into the nonvolatile memory 56 in association with the image data of the affected area image. The system control unit 50 can record the medical information into the recording medium 200 instead of the nonvolatile memory 56. In the present example embodiment, the system control unit 50 associates the medical information, as the attribute information of the image data, with the image data by storing the medical information into an image file in which the image data is recorded.

In step S904, the system control unit 50 transmits an image file including the image data of the affected area image and the medical information to the in-hospital system 1502 via the communication unit 54. While, in the present example embodiment, the medical information is included in the image file, the medical information can be stored as a file different from the image data, and the image file and the medical information file can be transmitted in association with each other.

In step S905, the system control unit 50 stores image file information and a "transmitting" status into the image transmission list stored in the nonvolatile memory 56. An image file name is used as an example of image file information to be stored.

In the above-described manner, in the affected area image capturing processing, an affected area image is captured and the captured affected area image data and medical information are transmitted to the in-hospital system 1502 in association with each other.

<Affected Area Image Confirmation Processing>

Figure 10:
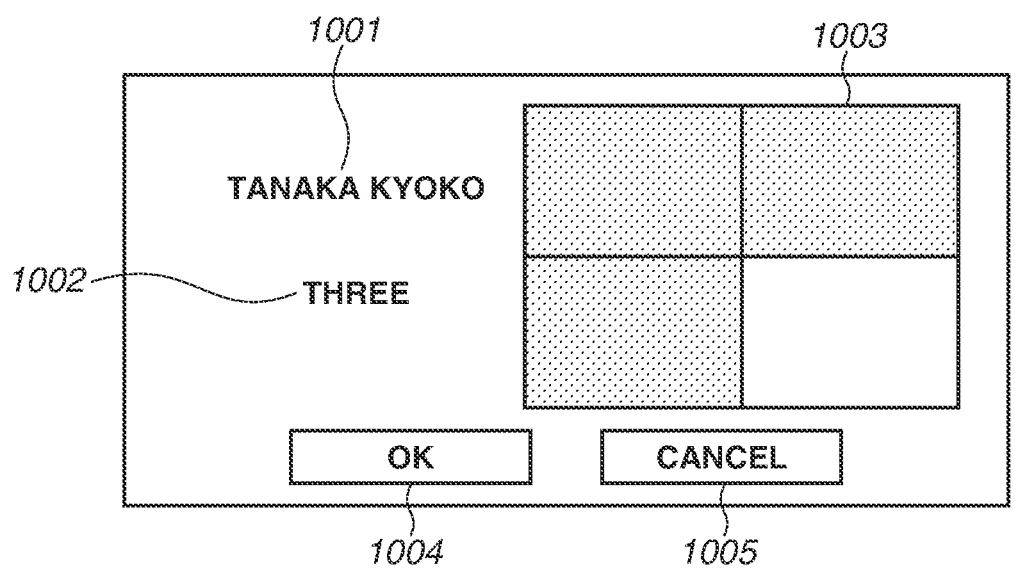
FIG. 10 is a diagram illustrating an example of a screen that is displayed in affected area image confirmation processing.

FIG. 10 illustrates an example of a screen that is displayed in the affected area image confirmation processing in step S427 according to the present example embodiment.

FIG. 10 illustrates an example of an affected area image confirmation screen. On the affected area image confirmation screen, the user confirms set medical information and image data which has been captured in step S901 and of which transmission has not been completed.

An item 1001 displays patient information (patient name) from among pieces of medical information associated with image data that is in the "transmitting" status in the image transmission list. In a case where a plurality of pieces of image data is in the "transmitting" status, medical information associated with image data of an image captured first or last can be displayed. Alternatively, medical information of all pieces of image data can be displayed.

An item 1002 displays the number of pieces of image data that are in the "transmitting" status in the image transmission list.

An area 1003 displays thumbnail images of image data that is in the "transmitting" status in the image transmission list. In a case where a plurality of pieces of image data in the "transmitting" status exists, a thumbnail image of image data of an image captured first or last can be displayed, or thumbnail images of all pieces of image data can be displayed as illustrated in FIG. 10.

An OK button 1004 and a cancel button 1005 are used when the user selects OK or cancel after confirmation of the medical information and the thumbnail image.

Figure 11A:
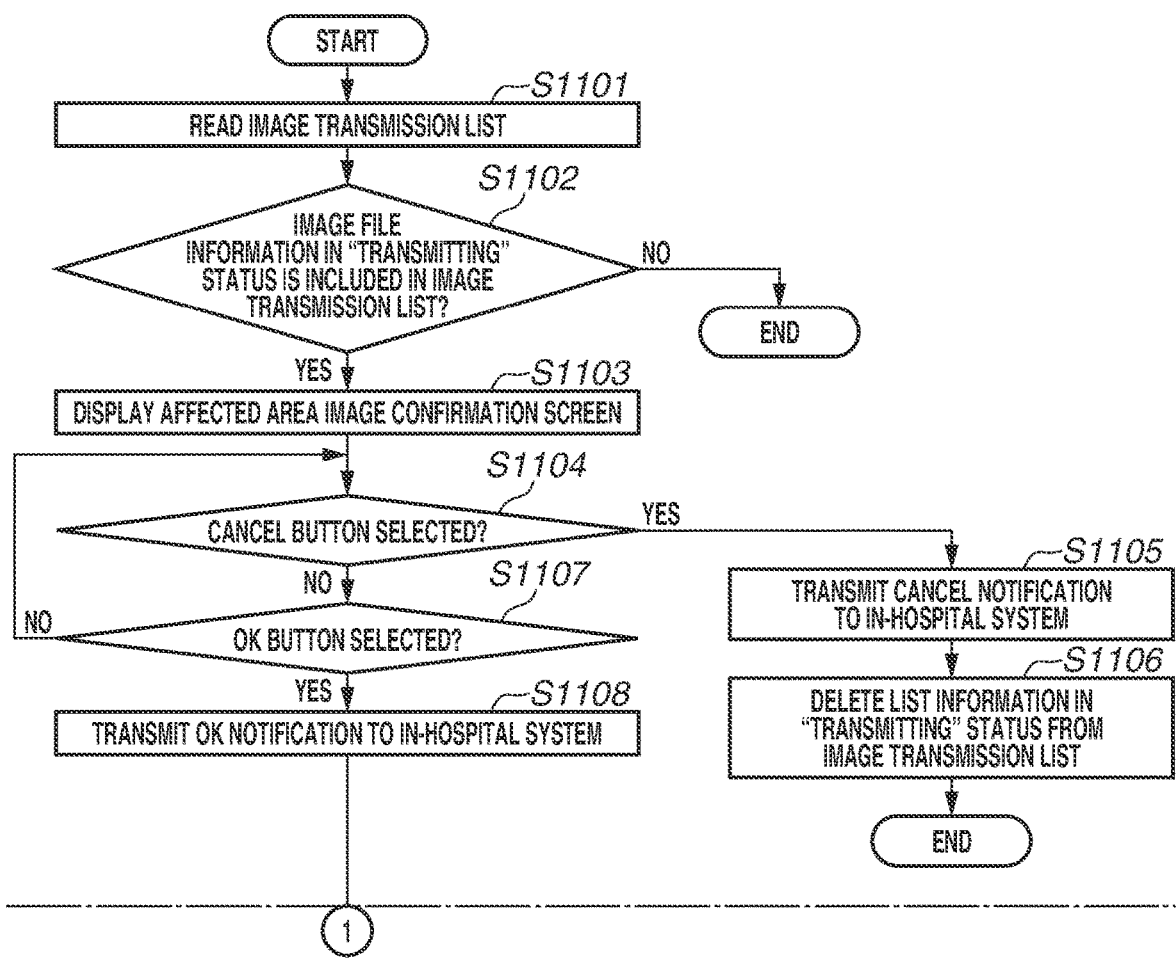
FIGS. 11A and 11B are flowcharts illustrating the affected area image confirmation processing.
Figure 11B:
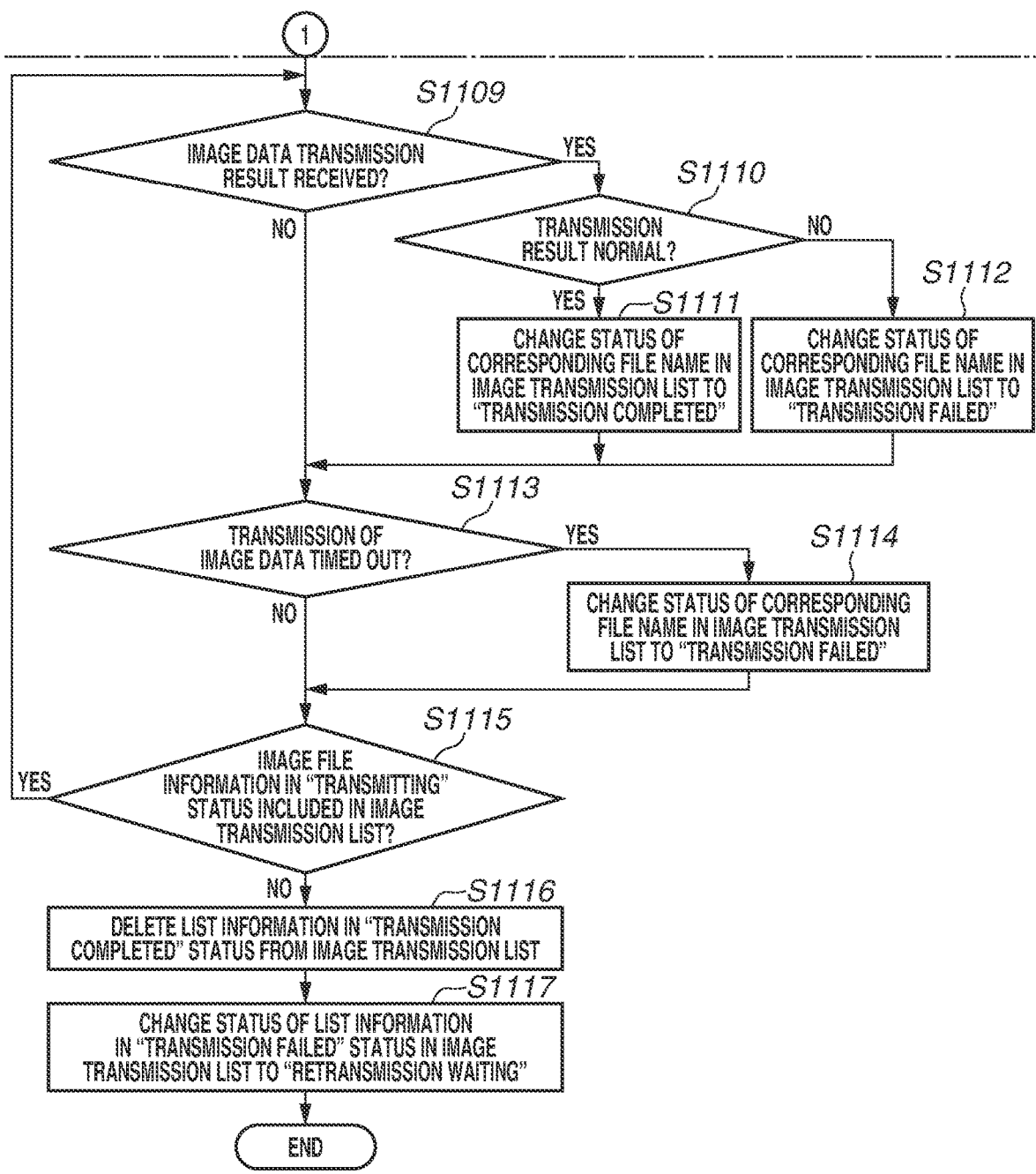

Hereinafter, the affected area image confirmation processing (step S427) will be described with reference to FIGS. 11A and 11B.

In step S1101, the system control unit 50 reads an image transmission list stored in the nonvolatile memory 56.

In step S1102, the system control unit 50 determines whether image file information in the "transmitting" status is included in the image transmission list acquired in step S1101. In a case where image file information in the "transmitting" status is included in the image transmission list (YES in step S1102), the processing proceeds to step S1103. In a case where image file information in the "transmitting" status is not included in the image transmission list (NO in step S1102), the processing ends.

In step S1103, the system control unit 50 displays the affected area image confirmation screen illustrated in FIG. 10.

In step S1104, the system control unit 50 determines whether the user has selected the cancel button 1005 on the affected area image confirmation screen. The selection is performed by a touching operation on the cancel button 1005 or a pressing operation on the SET button 75 in a state in which a selection frame is set on the cancel button 1005 by a dial operation or a cross key operation. In a case where the cancel button has been selected (YES in step S1104), the processing proceeds to step S1105. In a case where the cancel button has not been selected (NO in step S1104), the processing proceeds to step S1107.

In step S1105, the system control unit 50 transmits a cancel notification to the in-hospital system 1502 via the communication unit 54.

In step S1106, the system control unit 50 deletes, from the image transmission list stored in the nonvolatile memory 56, list information (image file information and status) that is in the "transmitting" status in the image transmission list.

In step S1107, the system control unit 50 determines whether the user has selected the OK button 1004 on the screen. The selection is performed by a touching operation on the OK button 1004 a pressing operation on the SET button 75 in a state in which a selection frame is set on the OK button 1004 by a dial operation or a cross key operation. In a case where the OK button 1004 has been selected (YES in step S1107), the processing proceeds to step S1108. In a case where the OK button 1004 has not been selected (NO in step S1107), the processing returns to step S1104.

In step S1108, the system control unit 50 transmits an OK notification to the in-hospital system 1502 via the communication unit 54.

In step S1109, the system control unit 50 determines whether a transmission result of the image data transmitted to the in-hospital system 1502 in step S904 has been received from the in-hospital system 1502. In a case where a transmission result of the image data has been received (YES in step S1109), the processing proceeds to step S1110. In a case where a transmission result has not been received (NO in step S1109), the processing proceeds to step S1113.

In step S1110, the system control unit 50 determines whether the image data transmission result received from the in-hospital system 1502 is normal. In a case where the transmission result is normal (YES in step S1110), the processing proceeds to step S1111. In a case where the transmission result is not normal (NO in step S1110), the processing proceeds to step S1112.

In step S1111, among pieces of image file information in the image transmission list stored in the nonvolatile memory 56, the system control unit 50 changes a status of image file information for which the transmission result has been received from the in-hospital system 1502, to "transmission completed".

In step S1112, among pieces of image file information in the image transmission list stored in the nonvolatile memory 56, the system control unit 50 changes a status corresponding to image file information for which the transmission result has been received from the in-hospital system 1502, to "transmission failed".

In step S1113, the system control unit 50 determines whether a transmission result has not been received from the in-hospital system 1502 for a certain period of time from when image data has been transmitted to the in-hospital system 1502 in step S904. In a case where the transmission has timed out (YES in step S1113), the processing proceeds to step S1114. In a case where the transmission has not timed out (NO in step S1113), the processing proceeds to step S1115.

In step S1114, among pieces of image file information in the image transmission list stored in the nonvolatile memory 56, the system control unit 50 changes a status of image file information for which the transmission result has not been received from the in-hospital system 1502, to "transmission failed".

In step S1115, the system control unit 50 determines whether list information in the "transmitting" status is included in the image transmission list. In a case where list information in the "transmitting" status is included (YES in step S1115), the processing returns to step S1109. In a case where list information in the "transmitting" status is not included (NO in step S1115), the processing proceeds to step S1116.

In step S1116, the system control unit 50 deletes list information that is in the "transmission completed" status, from the image transmission list stored in the nonvolatile memory 56.

In step S1117, the system control unit 50 changes a status of list information that is in the "transmission failed" status in the image transmission list stored in the nonvolatile memory 56, to "retransmission waiting".

In the above-described manner, in the affected area image confirmation processing, it is possible to check image data that has not been transmitted to the in-hospital system 1502, and it is also possible to cancel transmission of unsent image data. The processing in steps S1109 to S1117 is also executed in a case where image data (image file) transmission result from the in-hospital system 1502 is received, transmission time-out is occurred, and image data in the "transmitting" status is no more in the image transmission list, even when the affected area image retransmission processing is not executed. In other words, an image transmission list stored in the nonvolatile memory 56 is appropriately updated in accordance with a transmission status of image data.

<Affected Area Image Retransmission Processing>

FIGS. 12A to 12D each illustrate an example of a screen that is displayed in the affected area image retransmission processing.

Figure 12A:
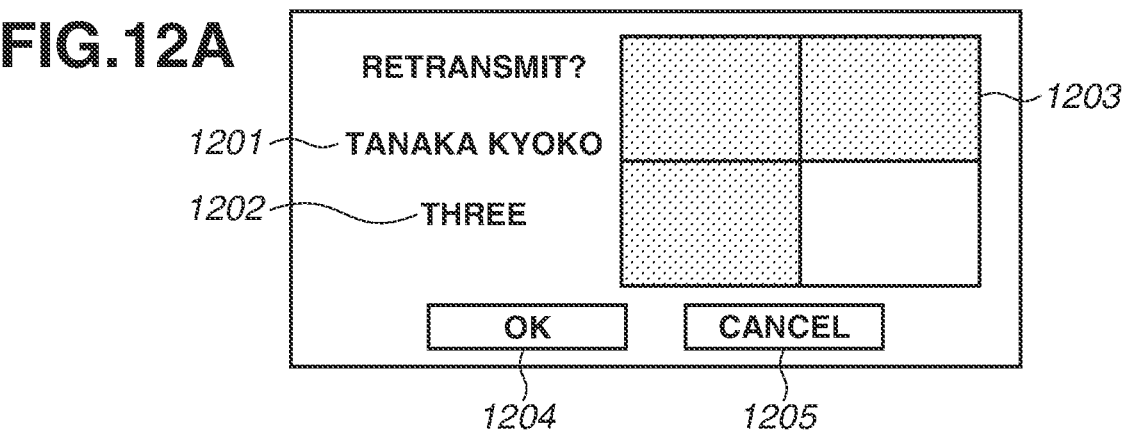
FIGS. 12A to 12D are diagrams each illustrating an example of a screen that is displayed in affected area image retransmission processing.

FIG. 12A illustrates a retransmission confirmation screen.

An item 1201 is patient information (patient name) associated with image data that is in the "retransmission waiting" status in the image transmission list. In a case where a plurality of pieces of image data in the "retransmission waiting" status exists, medical information associated with image data of an image captured first or last can be displayed, or medical information associated with all pieces of image data can be displayed.

An item 1202 displays the number of pieces of image data that are in the "retransmission waiting" status in the image transmission list.

An item 1203 is thumbnail images of image data that is in the "retransmission waiting" status in the image transmission list. In a case where a plurality of pieces of image data in the "retransmission waiting" status exists, a thumbnail image of image data of an image captured first or last can be displayed, or thumbnail images of all pieces of image data can be displayed as illustrated.

An OK button 1204 is used when the user selects OK after confirmation of whether to retransmit image data.

A cancel button 1205 is used when the user selects cancel after confirmation of whether to retransmit image data.

Figure 12B:
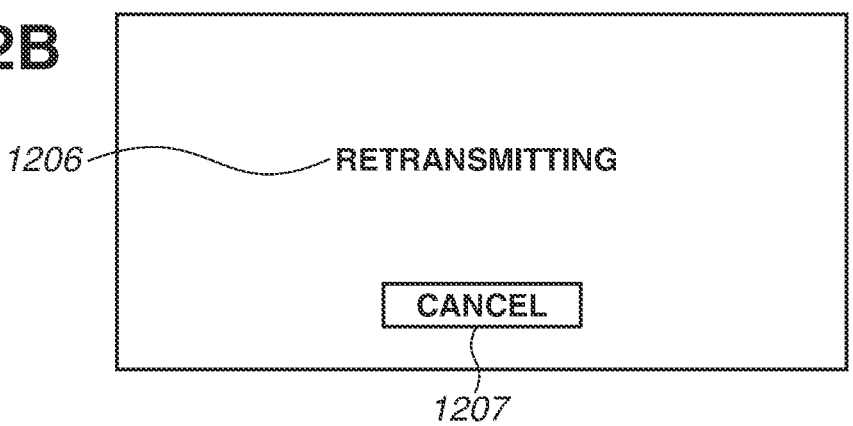

FIG. 12B illustrate a retransmitting screen.

On the retransmitting screen, a message 1206 notifying that image is being transmitted and a cancel button 1207 are displayed. The progress of the number of image data being transmitted out of pieces of image data can be displayed. A transmission stop instruction can be issued by operating the cancel button 1207.

Figure 12C:
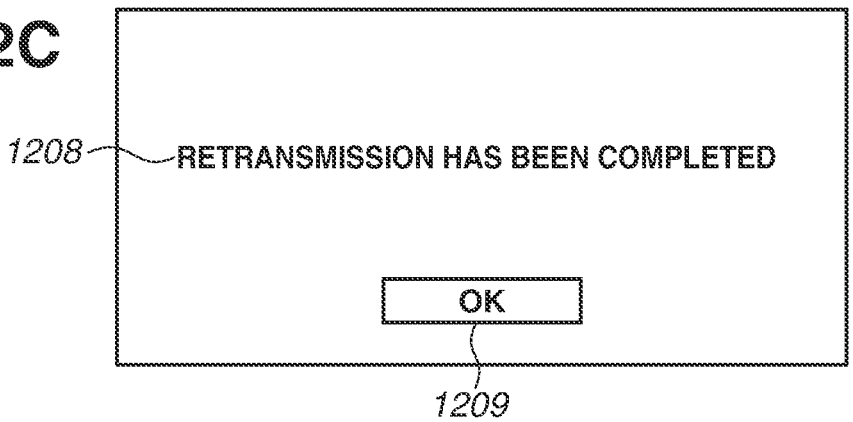

FIG. 12C is a retransmission success screen indicating that the retransmission has been properly performed.

On the retransmission success screen, a message 1208, notifying that the retransmission has succeeded, and an OK button 1209 are displayed.

Figure 12D:
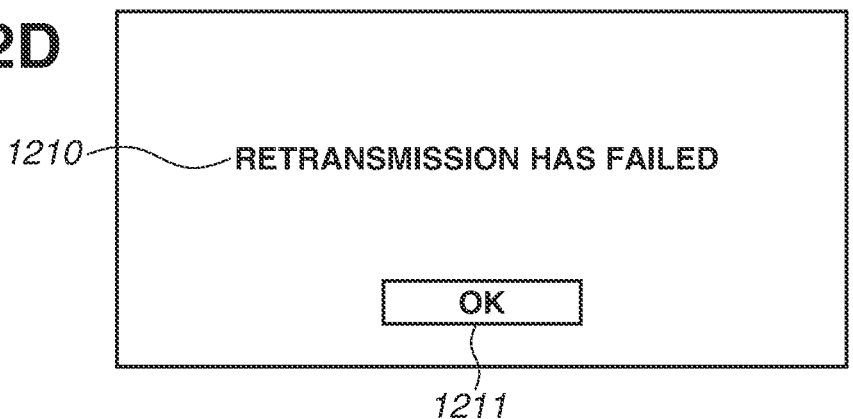

FIG. 12D is a retransmission failure screen notifying that retransmission has not been properly performed.

On the retransmission failure screen, a message 1210, notifying that the transmission has failed, and an OK button 1211 are displayed.

Figure 13:
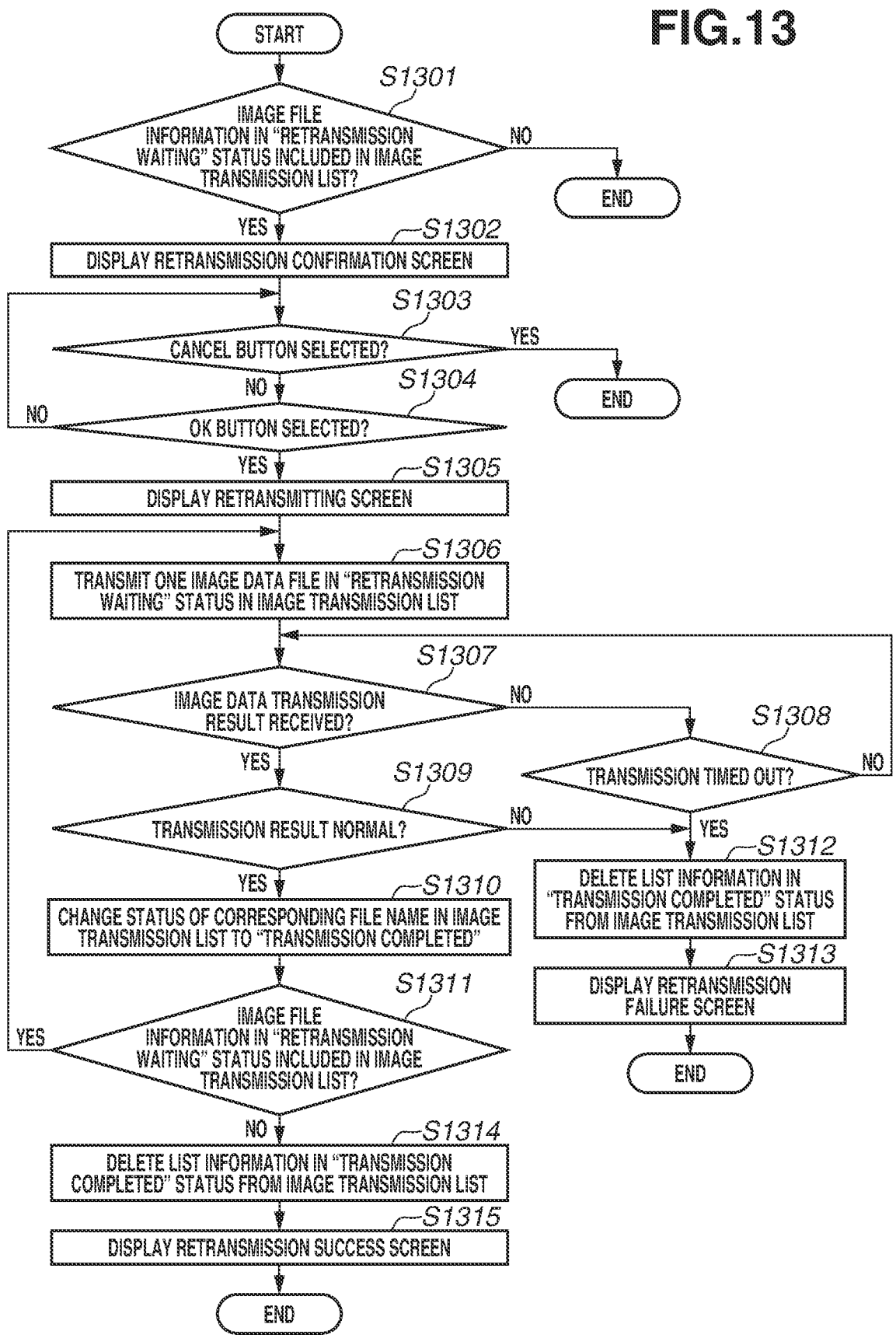
FIG. 13 is a flowchart of the affected area image retransmission processing.

Hereinafter, the affected area image retransmission processing (step S429) will be described with reference to FIG. 13.

In step S1301, the system control unit 50 determines whether list information in the "retransmission waiting" status is included in the image transmission list stored in the nonvolatile memory 56. In a case where list information in the "retransmission waiting" status is included in the image transmission list (YES in step S1301), the processing proceeds to step S1302. In a case where list information in the "retransmission waiting" status is not included in the image transmission list (NO in step S1301), the processing ends.

In step S1302, the system control unit 50 displays the retransmission confirmation screen illustrated in FIG. 12A.

In step S1303, the system control unit 50 determines whether the user has selected the cancel button 1205 on the screen. The selection is performed by a touching operation on the cancel button 1205 or a pressing operation on the SET button 75 in a state in which a selection frame is set on the cancel button 1205 by a dial operation or a cross key operation. In a case where the cancel button 1205 has been selected (YES in step S1303), the processing ends. In a case where the cancel button 1205 has not been selected (NO in step S1303), the processing proceeds to step S1304.

In step S1304, the system control unit 50 determines whether the user has selected the OK button 1204 on the screen. The selection is performed by a touching operation on the OK button 1204 or a pressing operation on the SET button 75 in a state in which a selection frame is set on the OK button 1204 by a dial operation or a cross key operation. In a case where the OK button 1204 has been selected (YES in step S1304), the processing proceeds to step S1305. In a case where the OK button 1204 has not been selected (NO in step S1304), the processing proceeds to step S1303.

In step S1305, the system control unit 50 displays the retransmitting screen illustrated in FIG. 12B.

In step S1306, the system control unit 50 transmits one image data file from among image data files that are in the "retransmission waiting" status in the image transmission list stored in the nonvolatile memory 56, to the in-hospital system 1502 via the communication unit 54. In a case of a configuration in which medical information associated with image data is data different from image data, data of the associated medical information is transmitted together.

In step S1307, the system control unit 50 determines whether a transmission result of image data transmitted to the in-hospital system 1502 in step S1306 has been received from the in-hospital system 1502. In a case where a transmission result has been received (YES in step S1307), the processing proceeds to step S1309. In a case where a transmission result has not been received (NO in step S1307), the processing proceeds to step S1308.

In step S1308, the system control unit 50 determines whether a transmission result has not been received from the in-hospital system 1502 for a certain period of time from when image data has been transmitted to the in-hospital system 1502 in step S1306. In a case where the transmission has timed out (YES in step S1308), the processing proceeds to step S1312. In a case where the transmission has not timed out (NO in step S1308), the processing returns to step S1307.

In step S1309, the system control unit 50 determines whether the transmission result received from the in-hospital system 1502 is normal. In a case where the transmission result is normal (YES in step S1309), the processing proceeds to step S1310. In a case where the transmission result is not normal (NO in step S1309), the processing proceeds to step S1312.

In step S1310, the system control unit 50 changes a status of image file information, for which the transmission result has been received from the in-hospital system 1502, in the image transmission list to "transmission completed".

In step S1311, the system control unit 50 determines whether list information in the "retransmission waiting" status is included in the image transmission list stored in the nonvolatile memory 56. In a case where list information in the "retransmission waiting" status is included in the image transmission list (YES in step S1311), the processing returns to step S1306. In a case where list information in the "retransmission waiting" status is not included in the image transmission list (NO in step S1311), the processing proceeds to step S1314.

In step S1312, the system control unit 50 deletes list information that is in the "transmission completed" status, from the image transmission list stored in the nonvolatile memory 56.

In step S1313, the system control unit 50 displays the retransmission failure screen illustrated in FIG. 12D.

In step S1314, the system control unit 50 deletes list information that is in the "transmission completed" status, from the image transmission list stored in the nonvolatile memory 56.

In step S1315, the system control unit 50 displays the retransmission success screen illustrated in FIG. 12C.

In the above-described manner, in the affected area image retransmission processing, unsent image data that is in the "retransmission waiting" status in the image transmission list can be retransmitted to the in-hospital system 1502.

<LV Display in Normal Image Capturing Mode>

As described above, in the medical mode, the LV display setting is switched between the imaging parameter display and the medical information display in accordance with an operation on the display switching button 83. In contrast to the configuration, in the normal image capturing mode (medical mode OFF), various LV display settings, such as ON/OFF of imaging parameter display, the type of imaging parameters to be displayed, ON/OFF of perpendicular display, and ON/OFF of live view display, can be switched in accordance with an operation on the display switching button 83. In the normal image capturing mode, the LV display setting is not switched to the medical information display even in a case where the display switching button 83 is operated.

In the medical mode, an imaging preparation operation, such as AF processing, AE processing, AWB processing, and EF processing, is executed in accordance with the first shutter switch signal SW1 (shutter button 61 half press) and by switching the LV display setting to the medical information display, the user is provided with medical information to perform a confirmation before affected area image capturing. In contrast to the configuration, in the normal image capturing mode, an imaging preparation operation is executed in accordance with the first shutter switch signal SW1, and the LV display is switched to LV display ON and display of specific imaging parameters (for example, AF frame (frame indicating an in-focus region), shutter speed, an aperture value). By hiding other imaging parameters and various types of information, a confirmation of live view and specific imaging parameters can be easily performed. For this reason, an imaging preparation operation can be executed before still image capturing in accordance with the second shutter switch signal SW2, and a live image captured after the imaging preparation operation can be confirmed, whereby it becomes possible to confirm imaging parameters important for still image capturing.

Other Example Embodiments

The above-described various types of control that are performed by the system control unit 50 can be performed by one piece of hardware. Alternatively, the entire apparatus can be controlled by a plurality of pieces of hardware (e.g., a plurality of processors or circuits) sharing the processing.

The example embodiments of the present invention have been described in detail, but the present invention is not limited to these specific example embodiments, and various configurations without departing from the scope of the invention are also included in the present invention. Furthermore, each of the above-described example embodiments merely indicates an example embodiment of the present invention, and the example embodiments can be appropriately combined.

In the above-described example embodiment, an example case where the present invention is applied to the imaging apparatus (digital camera) 100 has been described. An application example of the present invention is not limited to this example, and the present invention can be applied to any device including an imaging unit. More specifically, the present invention can be applied to a personal computer (PC), a personal digital assistance (PDA), a mobile phone terminal, a portable image viewer, a printer apparatus including a display, a digital photo frame, a music player, a game machine, and an electronic book reader.

An application example is not limited to an imaging apparatus main body, and the present invention can also be applied to a control apparatus that communicates with an imaging apparatus (including a network camera) via wired or wireless communication and remotely controls the imaging apparatus. Examples of the control apparatus that remotely controls the imaging apparatus include a smartphone, a tablet PC, and a desktop PC. By notifying commands for causing the imaging apparatus to perform various operations and settings, from the control apparatus based on operations performed by the control apparatus or processing performed by the control apparatus, the imaging apparatus can be remotely controlled. In addition, the control apparatus can receive a live view image captured by the imaging apparatus, via wired or wireless communication, and display the live view image.

An example embodiment of the present invention is also implemented by executing the following processing. More specifically, the processing is processing of supplying software (program) implementing the functions of the above-described example embodiment, to a system or an apparatus via a network or various storage media, and a computer (CPU, micro processing unit (MPU), etc.) of the system or the apparatus reading a program code and executing the program code. In this case, the program and a storage medium storing the program are included in the present invention.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to example embodiments, it is to be understood that the invention is not limited to the disclosed example embodiments and is defined by the following claims. The scope of the following claims is to be accorded the broadest interpretation so as to encompass all such modifications and equivalent structures and functions.

This application claims the benefit of Japanese Patent Application No. 2021-191533, filed Nov. 25, 2021, which is hereby incorporated by reference herein in its entirety.

What is claimed is:

1. An imaging apparatus comprising:
a memory and at least one processor which function as:
a display control unit configured to perform control to display, on a display unit, a live image captured by the imaging unit and medical information; and
a control unit configured to associate image data obtained by the imaging unit and the medical information in accordance with a full press operation on a shutter button,
wherein the display control unit performs control, in accordance with a predetermined user operation, to switch between first display of displaying the medical information together with a live image and second display of displaying an imaging parameter related to image capturing together with a live image, and
wherein the display control unit performs control, in accordance with a half press operation on the shutter button different from the predetermined user operation, to switch display to the first display.

2. The imaging apparatus according to claim 1, wherein the medical information includes at least one of patient information and region information.

3. The imaging apparatus according to claim 1, wherein the predetermined user operation is an operation on a specific operation member to which display switching is allocated.

4. The imaging apparatus according to claim 1, further comprising a controlling unit configured to perform control in such a manner that, in a case where the first display is performed, the medical information and/or the imaging parameter are changeable in accordance with a user operation, and in a case where the second display is performed, the medical information is not changeable in accordance with a user operation and the imaging parameter is changeable in accordance with a user operation.

5. The imaging apparatus according to claim 1, wherein the display control unit performs control to perform the first display while the shutter button is being half pressed.

6. The imaging apparatus according to claim 1, further comprising:
a switching unit configured to switch between a medical mode and a normal image capturing mode,
wherein, in a case where the medical mode is set, the display control unit switches display to the first display in accordance with a half press operation on the shutter button, and in a case where the normal image capturing mode is set, the display control unit does not switch display to the first display even when a half press operation on the shutter button is performed.

7. The imaging apparatus according to claim 6, wherein, in a case where the normal image capturing mode is set, the display control unit performs control to display a specific imaging parameter in accordance with a half press operation on the shutter button.

8. The imaging apparatus according to claim 7, wherein the specific imaging parameter includes at least one of an in-focus region, a shutter speed, and an aperture value.

9. The imaging apparatus according to claim 6, wherein, in a case where the medical mode is set, the display control unit performs control to switch between the first display and the second display in accordance with the predetermined user operation, and in a case where the normal image capturing mode is set, the display control unit performs control not to switch display to the first display in accordance with the predetermined user operation.

10. The imaging apparatus according to claim 6, wherein the display control unit performs control to perform the first display when switching to the medical mode is performed.

11. The imaging apparatus according to claim 1, wherein the control unit performs control to record the image data and the medical information into a recording medium such that the image data is associated with the medical information.

12. The imaging apparatus according to claim 1, further comprising:
a communication unit configured to communicate with a predetermined medical system,
wherein the display control unit performs control to display medical information acquired from the predetermined medical system.

13. The imaging apparatus according to claim 12, wherein the control unit transmits the image data and the medical information associated with the image data to a medical system.

14. The imaging apparatus according to claim 12,
wherein the communication unit communicates with a predetermined server, and
wherein the display control unit performs control to display medical information acquired from the predetermined medical system via the predetermined server.

15. The imaging apparatus according to claim 12, wherein the control unit performs control to acquire the medical information from the predetermined medical system, based on a code image captured by the imaging unit and to associate the acquired medical information and the image data.

16. A control method of an imaging apparatus including an imaging unit, the control method comprising:
displaying, as first display control, a live image captured by the imaging unit and medical information on a display unit;
associating image data obtained by the imaging unit and the medical information, in accordance with a full press operation on a shutter button;
switching, as second display control, between first display of displaying the medical information together with a live image and second display of displaying an imaging parameter related to image capturing, together with a live image, in accordance with a predetermined user operation; and
performing control, as third display control, to switch display to the first display in accordance with a half press operation on the shutter button that is different from the predetermined user operation.

17. A non-transitory computer-readable storage medium storing a program for causing a computer to execute the control method of an imaging apparatus according to claim 16.

* * * * *